US008236523B2

(12) United States Patent
Zhang et al.

(10) Patent No.: US 8,236,523 B2
(45) Date of Patent: Aug. 7, 2012

(54) CAMP REPORTERS AND HIGH THROUGHPUT ASSAYS

(75) Inventors: Jin Zhang, Baltimore, MD (US); Lisa Marie DiPilato, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 16 days.

(21) Appl. No.: 11/586,707

(22) Filed: Oct. 26, 2006

(65) Prior Publication Data

US 2007/0111270 A1 May 17, 2007

Related U.S. Application Data

(63) Continuation-in-part of application No. PCT/US2005/030099, filed on Aug. 23, 2005.

(60) Provisional application No. 60/603,623, filed on Aug. 23, 2004, provisional application No. 60/681,923, filed on May 17, 2005, provisional application No. 60/730,583, filed on Oct. 27, 2005.

(51) Int. Cl.
*C12P 21/06* (2006.01)
*C12N 1/00* (2006.01)

(52) U.S. Cl. ...... 435/69.1; 435/243; 435/69.7; 435/69.8

(58) Field of Classification Search .................. None
See application file for complete search history.

(56) References Cited

U.S. PATENT DOCUMENTS

| 5,981,200 | A | 11/1999 | Tsien et al. | |
|---|---|---|---|---|
| 6,197,928 | B1 | 3/2001 | Tsien et al. | |
| 6,573,059 | B1 | 6/2003 | Reymond | |
| 6,900,304 | B2 * | 5/2005 | Tsien et al. | ............ 536/23.4 |
| 2002/0137115 | A1 | 9/2002 | Umezawa | |
| 2003/0186229 | A1 | 10/2003 | Tsien | |
| 2005/0026234 | A1 | 2/2005 | Violin | |
| 2005/0054573 | A1 | 3/2005 | Werner | |
| 2006/0112440 | A1 | 5/2006 | Tsien et al. | |

FOREIGN PATENT DOCUMENTS

EP 1 687 441 8/2006

OTHER PUBLICATIONS

Roessel et al Imaging into the future: visualizing gene expression and protein interaction with fluorescent proteins. Nature cell Biology, vol. 4, Jan. 2002.*
Qiao et al. Cell-cycle dependent sub-cellular localization of exchange factor directly activated by cAMP. JBC 2002, vol. 277, No. 29, p. 26581-26586.*
Sato et al. Fluorescent indicators for cyclic GMP based on cyclic GMP-dependent protein kinase Iα and green fluorescent proteins. Anal. Chem. 72, 5918-5924, 2000.*
Honda et al and Dostmann et al Spatiotemporal dynamics of guanosine 3',5'-cyclic monophosphate revealed by a genetically encoded, fluorescent indicator. Proc. Natl. Acad. Sci. USA 98, 2437-2442 (2001).*
Kurokawa et al Visualizing the Signal Transduction Pathways in Living Cells with GFP-Based FRET Probes.((Acta Histochem Cytochem 37 (6):347-355, 2004.*
Rooij et al (Mechanism of regulation of the Epac1 family of cAMP dependent RapGEFs (J. Biol. Chem. 2000, 27: 20829-20836.*
Qiao et al. (Cell Cycle-dependent Sub-cellular Localization of Exchange Factor Directly Activated by cAMP J. Biol. Chem. 2002 277: 26581-26586. First Published on May 8, 2002.*
Peter Van Roessel et al. Imaging into the future: visualizing gene expression and protein interactions with fluorescent proteins. (Nature cell biology vol. 4, pp. 15-20 Jan. 2002).*
Rooij et al Mechanism of regulation of the Epac family of cAMP-dependent RapGEFs. J Biol Chem. Jul. 7, 2000;275(27):20829-36.*
Ensernik et al. A Novel Epac-specific cAMP analogue demonstrates independent regulation of Eap1 and ERK. Published on line Oct. 28, 2002 Nature Cell Biology.*
Honda et al (Spatiotemporal dynamics of guanosine 3',5'-cyclic monophosphate revealed by a genetically encoded, fluorescent indicator PNAS vol. 98, No. 5, 2437-2442.*
Viacheslav O. Nikolaev and Martin J. Lohse, Monitoring of cAMP Synthesis and Degradation in Living Cells, Emerging Technologies, Physiology vol. 21, 86-92, Apr. 2006.
Ponsioen et al., Detecting cAMP-induced Epac activation by fluorescence resonance energy transfer: Epac as a novel cAMP indicator, EMBO reports vol. 5, 1176-1180, 2004.
Violin et al., "A Genetically Encoded Fluorescent Reporter Reveals Oscillatory Phosphorylation by Protein Kinase C," *J. Cell Biol.* 161, 899-909, Jun. 9, 2003.
Zaccolo et al., "A Genetically Encoded, fluorescent Indicator for Cyclic AMP in Living Cells," *Nature Cell Biology* 2, 25-29, Jan. 2000.
De Rooij et al., "Mechanism of Regulation of the Epac Family of cAMP-dependent RapGEFs," *J. Biol. Chem.* 275, 20829-36, 2000.
Domin et al., "Linked Fluorophores FRET Calibration and FRET Studies of the Cyclin-CDK Switch in Mammalian Cells," *Prog. Biomed. Optics and Imaging, Proc. SPIE*, vol. 5139, 2003, pp. 238-242.
Evellin et al., "Measuring dynamic changes in cAMP using fluorescence resonance energy transfer," *Methods Mol. biol.* 284, 259-70, 2004.
Honda et al., "Spatiotemporal dynamics of guanosine 3',5'-cyclic monophosphate revealed by a genetically encoded, fluorescent indicator," *Proc. Natl. Acad. Sci. USA* 98, 437-42, Feb. 27, 2001.
Landa et al., "Interplay of $Ca^{2+}$ and cAMP Signaling in the Insulin-secreting MIN6β-Cell Line," *J. Biol. Chem. Papers in Press*, Jun. 29, 2005, pp. 1-19.
Mongillo et al., "Fluorescence Resonance Energy Transfer-Based Analysis of cAMP Dynamics in Live Neonatal Rat Cardiac Myocytes Reveals Distinct Functions of Compartmentalized Phosphodiesterases," *Cir. Res.* 95, 67-75, Jul. 9, 2004.
Nagai et al., "Expanded dynamic range of fluorescent indicators for $Ca^{2+}$ by circularly permuted yellow fluorescent proteins," *Proc. Natl. Acad. Sci. USA* 101, 10554-59, Jul. 20, 2004.
Nikolaev et al., "Novel Single Chain cAMp Sensors for Receptor-induced Signal Propagation," *J. Biol. Chem.* 279, 37215-18, 2004 (e-published Jul. 1, 2004).

(Continued)

*Primary Examiner* — Kagnew H Gebreyesus
(74) *Attorney, Agent, or Firm* — Banner & Witcoff, Ltd.

(57) ABSTRACT cAMP reporters useful for obtaining measurements of cAMP levels with high spatial and temporal resolution and in high throughput assays.

51 Claims, 13 Drawing Sheets
(2 of 13 Drawing Sheet(s) Filed in Color)

OTHER PUBLICATIONS

Polit et al., "Steady-state and time-resolved fluorescence studies of conformational changes induced by cyclic AMP and DNA binding to cyclic AMP receptor protein from *Escherichia coli*," *Eur. J. Biochem.* 270, 1413-23, 2003.

Rehmann et al., "Structure and regulation of the cAMP-binding domains of Epac2," *Nature Structural Biol.* 10, 26-32, Jan. 2003.

Santangelo et al., "Dual FRET molecular beacons for mRNA detection in living cells," *Nucl. Acids Res. 32*, 1-9, Apr. 14, 2004.

Zaccolo, "Use of chimeric fluorescent proteins and fluorescence resonance energy transfer to monitor cellular responses," *Circ. Res. 94*, 866-73, Apr. 16, 2004.

Zang et al., "Genetically encoded reporters of protein kinase A activity reveal impact of substrate tethering," *Proc. Natl. Acad. Sci. USA* 98, 14997-15002, 2001.

Dipilato et al., "Fluorescent indicators of cAMP and Epac activation reveal differential dynamics of cAMP signaling within discrete subcellular compartments," Proceedings of the National Academy of Sciences of the United States of America, vol. 101, No. 47, pp. 16513-16518, Nov. 23, 2004.

Filippin et al., "Stable interactions between mitochondria and endoplasmic reticulum allow rapid accumulation of calcium in a subpopulation of mitochondria," Journal of Biological Chemistry, American Society of Biolochemical Biologists, Birmingham, US, vol. 278, No. 40, pp. 39224-39234, Oct. 3, 2003.

Search Report and Opinion for EP 05808843.6 dated Oct. 15, 2009.

Hires et al., "Optical measurement of synaptic glutamate spillover and reuptake by linker optimized glutamate-sensitive fluorescent reporters," Proc Natl Acad Sci U S A. Mar. 18, 2008;105(11):4411-6. Epub Mar. 10, 2008.

Allen & Zhang, "Subcellular dynamics of protein kinase A activity visualized by FRET-based reporters," *Biochem. Biophys. Res. Commun. 348*, 716-21, 2006.

* cited by examiner

SEQUENCE LISTING

<160> NUMBER OF SEQ ID NOS: 21

<210> SEQ ID NO 1
<211> LENGTH: 881
<212> TYPE: PRT
<213> ORGANISM: Homo sapiens

<400> SEQUENCE: 1

```
Met Val Leu Arg Arg Met His Arg Pro Arg Ser Cys Ser Tyr Gln Leu
  1               5                  10                  15

Leu Leu Glu His Gln Arg Pro Ser Cys Ile Gln Gly Leu Arg Trp Thr
             20                  25                  30

Pro Leu Thr Asn Ser Glu Glu Ser Leu Asp Phe Ser Glu Ser Leu Glu
         35                  40                  45

Gln Ala Ser Thr Glu Arg Val Leu Arg Ala Gly Arg Gln Leu His Arg
     50                  55                  60

His Leu Leu Ala Thr Cys Pro Asn Leu Thr Arg Asp Arg Lys Tyr His
 65                  70                  75                  80

Leu Arg Leu Tyr Arg Gln Cys Cys Ser Gly Arg Glu Leu Val Asp Gly
                 85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
            115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
    210                 215                 220

Ser Lys Ala Gly Thr Val Leu Phe Ser Gln Gly Asp Lys Gly Thr Ser
225                 230                 235                 240
```

```
Trp Tyr Ile Ile Trp Lys Gly Ser Val Asn Val Thr His Gly Lys
            245                 250                 255

Gly Leu Val Thr Thr Leu His Glu Gly Asp Asp Phe Gly Gln Leu Ala
                260                 265                 270

Leu Val Asn Asp Ala Pro Arg Ala Ala Thr Ile Ile Leu Arg Glu Asp
            275                 280                 285

Asn Cys His Phe Leu Arg Val Asp Lys Gln Asp Phe Asn Arg Ile Ile
            290                 295                 300

Lys Asp Val Glu Ala Lys Thr Met Arg Leu Glu Glu His Gly Lys Val
305                 310                 315                 320

Val Leu Val Leu Glu Arg Ala Ser Gln Gly Ala Gly Pro Ser Arg Pro
                325                 330                 335

Pro Thr Pro Gly Arg Asn Arg Tyr Thr Val Met Ser Gly Thr Pro Glu
                340                 345                 350

Lys Ile Leu Glu Leu Leu Glu Ala Met Gly Pro Asp Ser Ser Ala
            355                 360                 365

His Asp Pro Thr Glu Thr Phe Leu Ser Asp Phe Leu Leu Thr His Arg
            370                 375                 380

Val Phe Met Pro Ser Ala Gln Leu Cys Ala Ala Leu Leu His His Phe
385                 390                 395                 400

His Val Glu Pro Ala Gly Gly Ser Glu Gln Glu Arg Ser Thr Tyr Val
                405                 410                 415

Cys Asn Lys Arg Gln Gln Ile Leu Arg Leu Val Ser Gln Trp Val Ala
            420                 425                 430

Leu Tyr Gly Ser Met Leu His Thr Asp Pro Val Ala Thr Ser Phe Leu
            435                 440                 445

Gln Lys Leu Ser Asp Leu Val Gly Arg Asp Thr Arg Leu Ser Asn Leu
450                 455                 460

Leu Arg Glu Gln Trp Pro Glu Arg Arg Cys His Arg Leu Glu Asn
465                 470                 475                 480

Gly Cys Gly Asn Ala Ser Pro Gln Met Lys Ala Arg Asn Leu Pro Val
                485                 490                 495

Trp Leu Pro Asn Gln Asp Glu Pro Leu Pro Gly Ser Ser Cys Ala Ile
                500                 505                 510

Gln Val Gly Asp Lys Val Pro Tyr Asp Ile Cys Arg Pro Asp His Ser
            515                 520                 525

Val Leu Thr Leu Gln Leu Pro Val Thr Ala Ser Val Arg Glu Val Met
530                 535                 540

Ala Ala Leu Ala Gln Glu Asp Gly Trp Thr Lys Gly Gln Val Leu Val
545                 550                 555                 560

Lys Val Asn Ser Ala Gly Asp Ala Ile Gly Leu Gln Pro Asp Ala Arg
                565                 570                 575

Gly Val Ala Thr Ser Leu Gly Leu Asn Glu Arg Leu Phe Val Val Asn
                580                 585                 590

Pro Gln Glu Ala His Glu Leu Ile Pro His Pro Asp Gln Leu Gly Pro
            595                 600                 605

Thr Val Gly Ser Ala Glu Gly Leu Asp Leu Val Ser Ala Lys Asp Leu
            610                 615                 620

Ala Gly Gln Leu Thr Asp His Asp Trp Ser Leu Phe Asn Ser Ile His
625                 630                 635                 640

Gln Val Glu Leu Ile His Tyr Val Leu Gly Pro Gln His Leu Arg Asp
            645                 650                 655

Val Thr Thr Ala Asn Leu Glu Arg Phe Met Arg Arg Phe Asn Glu Leu
            660                 665                 670
```

```
Gln Tyr Trp Val Ala Thr Glu Leu Cys Leu Cys Pro Val Pro Gly Pro
            675                 680                 685

Arg Ala Gln Leu Leu Arg Lys Phe Ile Lys Leu Ala Ala His Leu Lys
        690                 695                 700

Glu Gln Lys Asn Leu Asn Ser Phe Phe Ala Val Met Phe Gly Leu Ser
705                 710                 715                 720

Asn Ser Ala Ile Ser Arg Leu Ala His Thr Trp Glu Arg Leu Pro His
                725                 730                 735

Lys Val Arg Lys Leu Tyr Ser Ala Leu Glu Arg Leu Leu Asp Pro Ser
            740                 745                 750

Trp Asn His Arg Val Tyr Arg Leu Ala Leu Ala Lys Leu Ser Pro Pro
        755                 760                 765

Val Ile Pro Phe Met Pro Leu Leu Leu Lys Asp Met Thr Phe Ile His
    770                 775                 780

Glu Gly Asn His Thr Leu Val Glu Asn Leu Ile Asn Phe Glu Lys Met
785                 790                 795                 800

Arg Met Met Ala Arg Ala Ala Arg Met Leu His His Cys Arg Ser His
                805                 810                 815

Asn Pro Val Pro Leu Ser Pro Leu Arg Ser Arg Val Ser His Leu His
            820                 825                 830

Glu Asp Ser Gln Val Ala Arg Ile Ser Thr Cys Ser Glu Gln Ser Leu
        835                 840                 845

Ser Thr Arg Ser Pro Ala Ser Thr Trp Ala Tyr Val Gln Gln Leu Lys
850                 855                 860

Val Ile Asp Asn Gln Arg Glu Leu Ser Arg Leu Ser Arg Glu Leu Glu
865                 870                 875                 880

Pro

<210> SEQ ID NO 2
<211> LENGTH: 2646
<212> TYPE: DNA
<213> ORGANISM: Homo sapiens

<400> SEQUENCE: 2
atggtgttga gaaggatgca ccggccccga agctgctcct accagctgct gctggagcac       60
cagcgtccga gctgcatcca ggggctgcgc tggacaccac tcaccaacag cgaggagtcc      120
ctggatttca gcgagagcct ggagcaggcc tccacagagc gggtgctcag gctggggagg      180
cagctgcatc ggcatctgct ggccaccctg ccaaacctca cccgagaccg gaagtaccac      240
cttaggctct atcggcagtg ctgctctggc cgggagctgg tggatgggat cttggccctg      300
ggacttgggg tccattcccg gagccaagtt gtgggaatct gccaggtgct gctggatgaa      360
ggtgccctct gccatgtgaa acacgactgg gccttccagg accgagatgc ccaattctac      420
cggttccccg ggcccgagcc cgagcccgtg gaactcatg agatggagga ggagttggcc       480
gaagctgtgg ccctgctctc ccagcggggg cctgacgccc tgctcactgt ggcacttcga      540
aagcccccag tcagcgcac ggatgaagag ctggacctca tctttgagga gctgctgcac       600
atcaaggctg tggcccacct ctccaactcg gtgaagcgag aattagcggc tgttctgctc      660
tttgaaccac acagcaaggc agggaccgtg ttgttcagcc aggggggacaa gggcacttcg      720 tggtacatta tctggaaggg atctgtcaac gtggtgaccc atggcaaggg gctggtgacc      780
accctgcatg agggagatga ttttggacag ctggctctgg tgaatgatgc accccgggca      840
gccaccatca tcctgcgaga agacaactgt catttcctgc gtgtggacaa gcaggacttc      900
aaccgtatca tcaaggatgt ggaggcaaag accatgcggc tggaagaaca tggcaaagtg      960
```

```
gtgctggtgc tggagagagc ctctcagggc gccggcccttc ccgaccccc aaccccaggc    1020 aggaaccggt atacagtgat gtctggcacc ccagagaaga tcctagagct tctgttggag    1080
gccatgggac cagattccag tgctcatgac ccaacagaga cattcctcag cgacttcctc    1140
ctgacccaca gggtcttcat gcccagcgcc caactctgcg ctgcccttct gcaccacttc    1200
catgtggagc ctgcgggtgg cagcgagcag gagcgcagca cctacgtctg caacaagagg    1260
cagcagatct tgcggctggt cagccagtgg gtggccctgt atggctccat gctccacact    1320
gaccctgtgg ccaccagctt cctccagaaa ctctcagacc tggtgggcag ggacacccga    1380
ctcagcaacc tgctgaggga gcagtggcca gagaggcggc gatgccacag gttggagaat    1440
ggctgtggga atgcatctcc tcagatgaag gcccggaact tgcctgtttg ctccccaac     1500 caggacgagc cccttcctgg cagcagctgt gccatccaag ttggggataa agtcccctat    1560
gacatctgcc ggccagacca ctcagtgttg accctgcagc tgcctgtgac agcctccgtg    1620
agagaggtga tggcagcgtt ggcccaggag gatggctgga ccaaggggca ggtgctggtg    1680
aaggtcaatt ctgcaggtga tgccattggc ctgcagccag atgcccgtgg tgtggccaca    1740 tctctgggc tcaatgagcg tctctttgtt gtcaacccac aggaagcgca tgagctgatc      1800
ccacaccctg accagctggg gcccactgtg ggctctgctg aggggctgga cctggtgagt    1860
gccaaggacc tggcaggcca gctgacggac cacgactgga gcctcttcaa cagtatccac   1920
caggtggagc tgatccacta tgtgctgggc ccccagcatc tgcgggatgt caccaccgcc    1980
aacctggagc gcttcatgcg ccgcttcaat gagctgcagt actgggtggc caccgagctg    2040
tgtctctgcc ccgtgcccgg ccccgggcc cagctgctca ggaagttcat taagctggcg      2100
gcccacctca aggagcagaa gaatctcaat tccttctttg ccgtcatgtt tggcctcagc    2160
aactcggcca tcagccgcct agcccacacc tgggagcggc tgccccacaa agtccggaag   2220
ctgtactccg ccctcgagag gctgctggat ccctcatgga ccaccgggt ataccgactg       2280 gccctcgcca agctctcccc tcctgtcatc cccttcatgc cccttcttct caaagacatg    2340
accttcattc atgagggaaa ccacacacta gtggagaatc tcatcaactt gagaagatg      2400 agaatgatgg ccagagccgc gcggatgctg caccactgcc gaagccacaa ccctgtgcct    2460
ctctcaccac tcagaagccg agtttcccac ctccacgagg acagccaggt ggcgaggatt    2520
tccacatgct cggagcagtc cctgagcacc cggagtccag ccagcacctg gcttatgtc     2580 cagcagctga aggtcattga caaccagcgg gaactctccc gcctctcccg agagctggag    2640
ccatga                                                                2646
```

<210> SEQ ID NO 3
<211> LENGTH: 993
<212> TYPE: PRT
<213> ORGANISM: Mus musculus

<400> SEQUENCE: 3

```
Met Val Ala Ala His Ala Ala His Ser Gln Ser Ser Ala Glu Trp Ile
 1               5                  10                  15

Ala Cys Leu Asp Lys Arg Pro Leu Glu Arg Ser Ser Glu Asp Val Asp
                20                  25                  30

Ile Ile Phe Thr Arg Leu Lys Gly Val Lys Ala Phe Glu Lys Phe His
            35                  40                  45

Pro Asn Leu Leu Arg Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
 65                  70                  75                  80
```

-continued

```
Tyr Ala Val Leu Ala Gly Ser Leu Asp Val Lys Val Ser Glu Thr Ser
             85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Glu Asp Phe Lys
            130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
            165                 170                 175

Lys Glu Asn Val Pro Ser Glu Lys Ile Leu Arg Ala Gly Lys Ile Leu
            180                 185                 190

Arg Ile Ala Ile Leu Ser Arg Ala Pro His Met Ile Arg Asp Arg Lys
            195                 200                 205

Tyr His Leu Lys Thr Tyr Arg Gln Cys Cys Val Gly Thr Glu Leu Val
            210                 215                 220

Asp Trp Met Ile Gln Gln Thr Ser Cys Val His Ser Arg Thr Gln Ala
225                 230                 235                 240

Val Gly Met Trp Gln Val Leu Leu Glu Asp Gly Val Leu Asn His Val
            245                 250                 255

Asp Gln Glu Arg His Phe Gln Asp Lys Tyr Leu Phe Tyr Arg Phe Leu
            260                 265                 270

Asp Asp Glu Arg Glu Asp Ala Pro Leu Pro Thr Glu Glu Glu Lys Lys
            275                 280                 285

Glu Cys Asp Glu Glu Leu Gln Asp Thr Met Leu Leu Leu Ser Gln Met
290                 295                 300

Gly Pro Asp Ala His Met Arg Met Ile Leu Arg Lys Pro Pro Gly Gln
305                 310                 315                 320

Arg Thr Val Asp Asp Leu Glu Ile Ile Tyr Asp Glu Leu Leu His Ile
            325                 330                 335

Lys Ala Leu Ser His Leu Ser Thr Thr Val Lys Arg Glu Leu Ala Gly
            340                 345                 350

Val Leu Ile Phe Glu Ser His Ala Lys Gly Gly Thr Val Leu Phe Asn
            355                 360                 365

Gln Gly Glu Glu Gly Thr Ser Trp Tyr Ile Ile Leu Lys Gly Ser Val
            370                 375                 380

Asn Val Val Ile Tyr Gly Lys Gly Val Val Cys Thr Leu His Glu Gly
385                 390                 395                 400

Asp Asp Phe Gly Lys Leu Ala Leu Val Asn Asp Ala Pro Arg Ala Ala
            405                 410                 415

Ser Ile Val Leu Arg Glu Asp Asn Cys His Phe Leu Arg Val Asp Lys
            420                 425                 430

Glu Asp Phe Asn Arg Ile Leu Arg Asp Val Glu Ala Asn Thr Val Arg
            435                 440                 445

Leu Lys Glu His Asp Gln Asp Val Leu Val Leu Glu Lys Val Pro Ala
            450                 455                 460

Gly Asn Arg Ala Ala Asn Gln Gly Asn Ser Gln Pro Gln Gln Lys Tyr
465                 470                 475                 480

Thr Val Met Ser Gly Thr Pro Glu Lys Ile Leu Glu His Phe Leu Glu
            485                 490                 495

Thr Ile Arg Leu Glu Pro Ser Leu Asn Glu Ala Thr Asp Ser Val Leu
            500                 505                 510
```

```
Asn Asp Phe Val Met Met His Cys Val Phe Met Pro Asn Thr Gln Leu
        515                 520                 525
Cys Pro Ala Leu Val Ala His Tyr His Ala Gln Pro Ser Gln Gly Thr
    530                 535                 540
Glu Gln Glu Arg Met Asp Tyr Ala Leu Asn Asn Lys Arg Arg Val Ile
545                 550                 555                 560
Arg Leu Val Leu Gln Trp Ala Ala Met Tyr Gly Asp Leu Leu Gln Glu
                565                 570                 575
Asp Asp Val Ala Met Ala Phe Leu Glu Glu Phe Tyr Val Ser Val Ser
                580                 585                 590
Asp Asp Ala Arg Met Met Ala Ala Phe Lys Glu Gln Leu Pro Glu Leu
            595                 600                 605
Glu Lys Ile Val Lys Gln Ile Ser Glu Asp Ala Lys Ala Pro Gln Lys
        610                 615                 620
Lys His Lys Val Leu Leu Gln Gln Phe Asn Thr Gly Asp Glu Arg Ala
625                 630                 635                 640
Gln Lys Arg Gln Pro Ile Arg Gly Ser Asp Glu Val Leu Phe Lys Val
                645                 650                 655
Tyr Cys Ile Asp His Thr Tyr Thr Thr Ile Arg Val Pro Val Ala Ala
                660                 665                 670
Ser Val Lys Glu Val Ile Ser Ala Val Ala Asp Lys Leu Gly Ser Gly
            675                 680                 685
Glu Gly Leu Ile Ile Val Lys Met Asn Ser Gly Gly Glu Lys Val Val
        690                 695                 700
Leu Lys Ser Asn Asp Val Ser Val Phe Thr Thr Leu Thr Ile Asn Gly
705                 710                 715                 720
Arg Leu Phe Ala Cys Pro Arg Glu Gln Phe Asp Ser Leu Thr Pro Leu
                725                 730                 735
Pro Glu Gln Glu Gly Pro Thr Thr Gly Thr Val Gly Thr Phe Glu Leu
                740                 745                 750
Met Ser Ser Lys Asp Leu Ala Tyr Gln Met Thr Thr Tyr Asp Trp Glu
            755                 760                 765
Leu Phe Asn Cys Val His Glu Leu Glu Leu Ile Tyr His Thr Phe Gly
        770                 775                 780
Arg His Asn Phe Lys Lys Thr Thr Ala Asn Leu Asp Leu Phe Leu Arg
785                 790                 795                 800
Arg Phe Asn Glu Ile Gln Phe Trp Val Val Thr Glu Val Cys Leu Cys
                805                 810                 815
Ser Gln Leu Ser Lys Arg Val Gln Leu Lys Lys Phe Ile Lys Ile
            820                 825                 830
Ala Ala His Cys Lys Glu Tyr Lys Asn Leu Asn Ser Phe Phe Ala Ile
        835                 840                 845
Val Met Gly Leu Ser Asn Val Ala Val Ser Arg Leu Ala Leu Thr Trp
850                 855                 860
Glu Lys Leu Pro Ser Lys Phe Lys Lys Phe Tyr Ala Glu Phe Glu Ser
865                 870                 875                 880
Leu Met Asp Pro Ser Arg Asn His Arg Ala Tyr Arg Leu Thr Ala Ala
                885                 890                 895
Lys Leu Glu Pro Pro Leu Ile Pro Phe Met Pro Leu Leu Ile Lys Asp
                900                 905                 910
Met Thr Phe Thr His Glu Gly Asn Lys Thr Phe Ile Asp Asn Leu Val
            915                 920                 925
Asn Phe Glu Lys Met Arg Met Ile Ala Asn Thr Ala Arg Thr Val Arg
930                 935                 940
```

```
Tyr Tyr Arg Ser Gln Pro Phe Asn Pro Asp Ala Ala Gln Ala Asn Lys
945                 950                 955                 960

Asn His Gln Asp Val Arg Ser Tyr Val Arg Gln Leu Asn Val Ile Asp
            965                 970                 975

Asn Gln Arg Thr Leu Ser Gln Met Ser His Arg Leu Glu Pro Arg Arg
        980                 985                 990

Pro
```

<210> SEQ ID NO 4
<211> LENGTH: 2982
<212> TYPE: DNA
<213> ORGANISM: Mus musculus

<400> SEQUENCE: 4

| | | | | | |
|---|---|---|---|---|---|
| atggtcgctg | cgcacgctgc | acactctcag | tcctcggccg | agtggatcgc | ctgcctggat | 60 |
| aaaaggccgt | tggagcgatc | tagtgaagat | gtggacataa | ttttcacgcg | gctgaaagga | 120 |
| gttaaagctt | ttgagaaatt | tcacccaaac | ctccttcgtc | agatttgttt | atgcggttac | 180 |
| tatgagaacc | tggaaaaagg | aatcacactg | tttcgccaag | gggatattgg | aaccaactgg | 240 |
| tatgctgtcc | tggctgggtc | tttggatgtt | aaagtgtctg | agaccagcag | tcaccaggat | 300 |
| gcggtgacca | tctgcactct | gggaattggg | acagcctttg | agagtccat | tctggataac | 360 |
| accccctcgcc | atgcaaccat | cgttaccagg | agagcagcg | aacttctccg | cattgagcag | 420 |
| gaggacttca | aggcactatg | ggagaaatac | cgacagtata | tggccggact | tctggctcct | 480 |
| ccctatggtg | ttatggaaac | gggctctaac | aatgacagga | tcctgacaa | ggagaatgtc | 540 |
| ccttcagaga | agatcctcag | agctggaaaa | attttacgaa | ttgccattct | ctctcgagct | 600 |
| ccccacatga | taagagacag | aaagtaccac | ctaaagacat | acagacaatg | ctgtgttggg | 660 |
| actgagctgg | tagactggat | gatacagcag | acatcctgtg | ttcactcgcg | gactcaagct | 720 |
| gttggcatgt | ggcaagtctt | gctggaagat | ggtgtcctca | accatgtgga | ccaggagcgc | 780 |
| catttccaag | acaaatattt | attttatcga | tttctggatg | acgagcgtga | ggatgcccct | 840 |
| ttgcctactg | aggaagagaa | gaaggagtgt | gatgaagaac | ttcaggacac | catgctgctg | 900 |
| ctctcacaga | tgggccctga | cgcccacatg | agaatgatcc | tgcgaaaacc | acctggccag | 960 |
| aggactgtgg | atgacctaga | gattatctac | gacgagctcc | ttcatattaa | agccttatcc | 1020 |
| catctctcta | ccacagtgaa | acgggagtta | gcaggtgttc | tcattttga | gtctcacgcc | 1080 |
| aaaggaggaa | ctgtgttgtt | taaccagggg | gaagaaggta | cctcctggta | catcattctg | 1140 |
| aaaggatccg | tgaatgtagt | catttatggc | aagggtgtgg | tctgcaccct | gcacgaagga | 1200 |
| gatgactttg | gcaagttagc | tctagtgaac | gatgctccaa | gagctgcctc | cattgttctt | 1260 |
| cgggaagata | ttgtcacctt | cctaagagtc | gacaaggaag | acttcaatcg | gattctgagg | 1320 |
| gacgttgagg | cgaatacagt | cagacttaaa | gaacatgacc | aagatgtctt | ggtactggag | 1380 |
| aaggtcccag | cagggaacag | agctgctaat | caaggaaact | cacagcctca | gcaaaagtat | 1440 |
| actgtgatgt | caggaacacc | tgaaaagatt | ttagagcatt | ttctagaaac | aatacgcctt | 1500 |
| gagccatcgt | tgaatgaagc | aacagattcg | gttttaaatg | actttgttat | gatgcactgt | 1560 |
| gttttatgc | caaatacccca | gctttgccct | gcccttgtgg | cccattacca | cgcacagcct | 1620 |
| tctcaaggta | ccgagcagga | gagaatggat | tatgccctca | acaacaagag | gcgggtcatc | 1680 |
| cgcttggtcc | tgcagtgggc | ggccatgtat | ggcgatctcc | tccaagaaga | tgatgtggcc | 1740 |
| atggccttcc | tggaggagtt | ctatgtgtct | gtatcagatg | acgcacggat | gatggctgcc | 1800 |

-continued

```
ttcaaggagc agctgccaga gctggagaag attgtcaagc aaatctcaga agacgcaaaa    1860
gctccacaga agaagcacaa ggtgcttttg caacagttca acacaggtga cgagagggcc    1920
cagaagcgtc agcctattcg tggctctgat gaggttttgt tcaaggtcta ctgcatcgac    1980
cacacctata ctaccattcg tgtgccggta gctgcctcgg tgaaggaagt catcagtgca    2040
gtagctgaca aactgggctc aggggaaggc ctgatcatcg tcaagatgaa ctctggagga    2100
gaaaaggtgg tgctgaaatc taatgatgtt tcagtattta cgacgctcac cattaatgga    2160
cgcctgtttg cctgcccgag agagcaattc gactcactga ctcccttgcc ggaacaggaa    2220
ggcccgacca ctgggacagt gggaacattt gagctgatga gctcgaaaga cctggcgtac    2280
cagatgacaa cctacgattg ggaactcttc aactgtgtgc atgagctgga gctaatctac    2340
cacacatttg gaaggcataa ttttaaaaag accacggcaa acttggattt gttcctgagg    2400
aggtttaatg aaattcagtt ttgggttgtc actgaggtct gccttttgttc ccagctcagc    2460
aaacgtgttc agcttttgaa aaaatttatc aagatagcgg ctcactgcaa ggagtacaaa    2520
aatctaaatt cctttttcgc catcgtcatg ggactcagca acgtggccgt gagccgcttg    2580
gcactaacgt gggagaaaact gccgagcaag tttaagaagt tctatgcgga gtttgagagc    2640
ttgatggatc cttccagaaa ccacagggca tacaggctga cagcagccaa gctggagccc    2700
cctctcatcc ctttcatgcc cttgcttatt aaagatatga catttactca tgaggggaac    2760
aagacgttca ttgacaatct agtaaacttt gaaaaaatgc gcatgattgc aaacactgcc    2820
agaacagtac ggtactacag gagccagccc ttcaatccgg atgccgctca agctaataag    2880
aaccatcagg atgtccggag ttatgtacgg caattaaatg tgattgacaa ccagagaact    2940
ttatcacaga tgtcacacag attagagcct cgaaggccat ag                       2982
```

<210> SEQ ID NO 5
<211> LENGTH: 10
<212> TYPE: PRT
<213> ORGANISM: Homo sapiens
<220> FEATURE:
<223> OTHER INFORMATION: peptide linker

<400> SEQUENCE: 5

Pro Lys Lys Lys Arg Lys Val Glu Asp Ala
1               5                   10

<210> SEQ ID NO 6
<211> LENGTH: 13
<212> TYPE: PRT
<213> ORGANISM: Homo sapiens

<400> SEQUENCE: 6

Lys Lys Lys Lys Lys Ser Lys Thr Lys Cys Val Ile Met
1               5                   10

<210> SEQ ID NO 7
<211> LENGTH: 30
<212> TYPE: PRT
<213> ORGANISM: Homo sapiens

<400> SEQUENCE: 7

Met Ala Ile Gln Leu Arg Ser Leu Phe Pro Leu Ala Leu Pro Gly Met
1               5                   10                  15

Leu Ala Leu Leu Gly Trp Trp Trp Phe Phe Ser Arg Lys Lys
            20                  25                  30

```
<210> SEQ ID NO 8
<211> LENGTH: 16
<212> TYPE: PRT
<213> ORGANISM: Homo sapiens

<400> SEQUENCE: 8

Met Leu Ser Leu Arg Gly Ser Ile Arg Phe Phe Lys Arg Ser Gly Ile
1               5                   10                  15

<210> SEQ ID NO 9
<211> LENGTH: 225
<212> TYPE: PRT
<213> ORGANISM: Discosoma sp.

<400> SEQUENCE: 9

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 10
<211> LENGTH: 18
<212> TYPE: PRT
<213> ORGANISM: Artificial Sequence
<220> FEATURE:
<223> OTHER INFORMATION: peptide linker

<400> SEQUENCE: 10

Gly Ser Thr Ser Gly Ser Gly Lys Pro Gly Ser Gly Glu Gly Ser Thr
1               5                   10                  15

Lys Gly
```

```
<210> SEQ ID NO 11
<211> LENGTH: 238
<212> TYPE: PRT
<213> ORGANISM: Aequorea victoria

<400> SEQUENCE: 11

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 12
<211> LENGTH: 239
<212> TYPE: PRT
<213> ORGANISM: Aequorea victoria

<400> SEQUENCE: 12

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 13
<211> LENGTH: 239
<212> TYPE: PRT
<213> ORGANISM: Aequorea victoria

<400> SEQUENCE: 13

Met Val Ser Lys Gly Glu Glu Leu Phe Thr Gly Val Val Pro Ile Leu
  1               5                  10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

```
<210> SEQ ID NO 14
<211> LENGTH: 239
<212> TYPE: PRT
<213> ORGANISM: Aequorea victoria

<400> SEQUENCE: 14

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 15
<211> LENGTH: 6
<212> TYPE: PRT
<213> ORGANISM: Artificial Sequence
<220> FEATURE:
<223> OTHER INFORMATION: tetracysteine motif
<220> FEATURE:
<221> NAME/KEY: VARIANT
<222> LOCATION: (1)...(6)
<223> OTHER INFORMATION: Xaa = Any Amino Acid
<220> FEATURE:
<221> NAME/KEY: VARIANT
<222> LOCATION: (1)...(6)
<223> OTHER INFORMATION: Xaa = Any Amino Acid
<220> FEATURE:
<221> NAME/KEY: VARIANT
<222> LOCATION: (1)...(6)
<223> OTHER INFORMATION: Xaa = Any Amino Acid
<220> FEATURE:
<221> NAME/KEY: VARIANT
<222> LOCATION: (1)...(6)
<223> OTHER INFORMATION: Xaa = Any Amino Acid

<400> SEQUENCE: 15

Cys Cys Xaa Xaa Cys Cys
 1               5
```

<210> SEQ ID NO 16
<211> LENGTH: 31
<212> TYPE: DNA
<213> ORGANISM: Homo sapiens

<400> SEQUENCE: 16
cgcggtaccc ccgtgggaac tcatgagatg g                                    31

<210> SEQ ID NO 17
<211> LENGTH: 436
<212> TYPE: PRT
<213> ORGANISM: Rattus norvegicus
<220> FEATURE:
<221> NAME/KEY: misc_feature
<222> LOCATION: (1)...(0)
<223> OTHER INFORMATION: n = A,T,C or G

<400> SEQUENCE: 17

```
Arg Val Ile Arg Leu Val Leu Gln Trp Ala Ala Met Tyr Gly Asp Leu
 1               5                  10                  15

Leu Gln Glu Asp Asp Val Ala Met Ala Phe Leu Glu Glu Phe Tyr Val
             20                  25                  30

Ser Val Ser Asp Asp Ala Arg Met Met Val Ala Phe Lys Glu Gln Leu
         35                  40                  45

Ala Glu Leu Glu Lys Thr Val Lys Gln Ile Ser Glu Asp Ala Lys Ala
     50                  55                  60

Pro Gln Lys Lys His Lys Val Leu Leu Gln Gln Phe Asn Thr Gly Asp
 65                  70                  75                  80

Glu Arg Ala Gln Lys Arg Gln Pro Ile Arg Gly Ser Asp Glu Val Leu
                 85                  90                  95

Phe Lys Val Tyr Cys Ile Asp His Thr Asp Thr Thr Ile Arg Val Pro
            100                 105                 110

Val Ala Ala Ser Val Lys Glu Val Ile Ser Ala Val Ala Asp Lys Leu
        115                 120                 125

Gly Ser Gly Glu Gly Leu Ile Ile Val Lys Met Asn Ser Gly Gly Glu
    130                 135                 140

Lys Val Val Leu Lys Pro Asn Asp Val Ser Val Phe Thr Thr Leu Thr
145                 150                 155                 160

Ile Asn Gly Arg Leu Phe Ala Cys Pro Arg Glu Gln Phe Asp Ser Leu
                165                 170                 175

Thr Pro Leu Pro Glu Gln Glu Gly Pro Thr Gly Thr Val Gly Thr
            180                 185                 190

Phe Glu Leu Met Ser Ser Lys Asp Leu Ala Tyr Gln Met Thr Thr Tyr
        195                 200                 205

Asp Trp Glu Leu Phe Asn Cys Val Leu Glu Leu Glu Leu Ile Tyr His
    210                 215                 220

Thr Phe Gly Arg His Asn Phe Lys Lys Thr Thr Ala Asn Leu Asp Leu
225                 230                 235                 240

Phe Leu Arg Arg Phe Asn Glu Ile Gln Phe Trp Val Val Thr Glu Ile
                245                 250                 255

Cys Leu Cys Ser Gln Leu Ser Lys Arg Val Gln Leu Leu Lys Lys Cys
            260                 265                 270

Ile Lys Ile Ala Ala His Cys Lys Glu Tyr Lys Asn Leu Asn Ser Phe
        275                 280                 285

Phe Gly Ile Val Met Gly Leu Ser Asn Val Ala Glu Ser Arg Leu Ala
    290                 295                 300

Leu Thr Trp Glu Lys Leu Pro Ser Lys Phe Lys Lys Phe Tyr Ala Glu
305                 310                 315                 320
```

-continued

```
Phe Glu Ser Leu Met Asp Pro Ser Arg Asn His Lys Ala Tyr Arg Leu
                325                 330                 335

Thr Ala Ala Lys Leu Glu Pro Pro Leu Ile Pro Phe Met Pro Leu Leu
            340                 345                 350

Ile Lys Asp Met Thr Phe Thr His Glu Gly Asn Lys Thr Phe Ile Asp
        355                 360                 365

Asn Leu Val Asn Phe Glu Lys Met Arg Met Ile Ala Asn Thr Ala Arg
    370                 375                 380

Thr Val Arg Tyr Tyr Arg Ser Gln Pro Phe Asn Pro Asp Ala Ala Gln
385                 390                 395                 400

Ala Asn Lys Asn His Gln Asp Val Arg Ser Tyr Val Arg Gln Leu Asn
                405                 410                 415

Val Ile Asp Asn Gln Arg Thr Leu Ser Gln Met Ser His Arg Leu Glu
            420                 425                 430

Pro Arg Arg Pro
        435

<210> SEQ ID NO 18
<211> LENGTH: 931
<212> TYPE: PRT
<213> ORGANISM: Pongo pygmaeus

<400> SEQUENCE: 18

Met Val Ala Thr His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Gly Leu Leu Arg Ile Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Val Pro Ser Glu Lys Ile Leu Arg Ala Gly Lys Ile Leu
            180                 185                 190

Arg Asn Ala Ile Leu Ser Arg Ala Pro His Met Ile Arg Asp Arg Lys
        195                 200                 205

Tyr His Leu Lys Thr Tyr Arg Gln Cys Cys Val Gly Thr Glu Leu Val
    210                 215                 220

Asp Trp Met Met Gln Gln Thr Pro Cys Val His Ser Arg Thr Gln Ala
225                 230                 235                 240

Val Gly Met Trp Gln Val Leu Leu Glu Asp Gly Val Leu Asn His Val
                245                 250                 255
```

-continued

```
Asp Gln Glu His His Phe Gln Asp Lys Tyr Leu Phe Tyr Arg Phe Leu
            260                 265                 270

Asp Asp Glu Asn Glu Asp Ala Pro Leu Pro Thr Glu Glu Lys Lys
        275                 280                 285

Glu Cys Asp Glu Glu Leu Gln Asp Thr Met Leu Leu Leu Ser Gln Met
    290                 295                 300

Gly Pro Asp Ala His Met Arg Met Ile Leu Arg Lys Pro Pro Gly Gln
305                 310                 315                 320

Arg Thr Val Asp Asp Leu Glu Ile Ile Tyr Glu Glu Leu Leu His Ile
                325                 330                 335

Lys Ala Leu Ser His Leu Ser Thr Thr Val Lys Arg Glu Leu Ala Gly
            340                 345                 350

Val Leu Ile Phe Glu Ser His Ala Lys Gly Gly Thr Val Leu Phe Asn
        355                 360                 365

Gln Gly Glu Glu Gly Thr Ser Trp Tyr Ile Ile Leu Lys Gly Ser Val
    370                 375                 380

Asn Val Val Ile Tyr Gly Lys Gly Val Val Cys Thr Leu His Glu Gly
385                 390                 395                 400

Asp Asp Phe Gly Lys Leu Ala Leu Val Asn Asp Ala Pro Arg Ala Ala
                405                 410                 415

Ser Ile Val Leu Arg Glu Asp Asn Cys His Phe Leu Arg Val Asp Lys
            420                 425                 430

Glu Asp Phe Asn Arg Ile Leu Arg Asp Val Glu Ala Asn Thr Val Arg
        435                 440                 445

Leu Lys Glu His Asp Gln Asp Val Leu Val Leu Glu Lys Val Pro Ala
    450                 455                 460

Gly Asn Arg Ala Ser Asn Gln Gly Asn Ser Gln Pro Gln Gln Lys Tyr
465                 470                 475                 480

Thr Val Met Ser Gly Thr Pro Glu Lys Ile Leu Glu His Phe Leu Glu
                485                 490                 495

Thr Ile Arg Leu Glu Ala Thr Leu Asn Glu Ala Thr Asp Ser Val Leu
            500                 505                 510

Asn Asp Phe Ile Met Met His Cys Val Phe Met Pro Asn Thr Gln Leu
        515                 520                 525

Cys Pro Ala Leu Val Ala His Tyr His Ala Gln Pro Ser Gln Gly Thr
    530                 535                 540

Glu Gln Glu Lys Met Asp Tyr Ala Leu Asn Asn Lys Arg Arg Val Ile
545                 550                 555                 560

Arg Leu Val Leu Gln Trp Ala Ala Met Tyr Gly Asp Leu Leu Gln Glu
                565                 570                 575

Asp Asp Val Ser Met Ala Phe Leu Glu Glu Phe Tyr Val Ser Val Ser
            580                 585                 590

Asp Asp Ala Arg Met Ile Ala Ala Leu Lys Glu Gln Leu Pro Glu Leu
        595                 600                 605

Glu Lys Ile Val Lys Gln Ile Ser Glu Asp Ala Lys Ala Pro Gln Lys
    610                 615                 620

Lys His Lys Val Leu Leu Gln Gln Phe Asn Thr Gly Asp Glu Arg Ala
625                 630                 635                 640

Gln Lys Arg Gln Pro Ile Arg Gly Ser Asp Glu Val Leu Phe Lys Val
                645                 650                 655

Tyr Cys Met Asp His Thr Tyr Thr Thr Ile Arg Val Pro Val Ala Ala
            660                 665                 670

Ser Val Lys Glu Val Ile Ser Ala Val Ala Asp Lys Leu Gly Ser Gly
        675                 680                 685
```

```
Glu Gly Leu Ile Val Val Lys Met Ser Ser Gly Glu Lys Val Val
    690                 695                 700

Leu Lys Pro Asn Asp Val Ser Val Phe Thr Thr Leu Thr Ile Asn Gly
705                 710                 715                 720

Arg Leu Phe Ala Cys Pro Arg Glu Gln Phe Asp Ser Leu Thr Pro Leu
                725                 730                 735

Pro Glu Gln Glu Gly Pro Thr Val Gly Thr Val Gly Thr Phe Glu Leu
            740                 745                 750

Met Ser Ser Lys Asp Leu Ala Tyr Gln Met Thr Ile Tyr Asp Trp Glu
        755                 760                 765

Leu Phe Asn Cys Val His Glu Leu Glu Leu Ile Tyr His Thr Phe Gly
    770                 775                 780

Arg His Asn Phe Lys Lys Thr Thr Ala Asn Leu Asp Leu Phe Leu Arg
785                 790                 795                 800

Arg Phe Asn Glu Ile Gln Phe Trp Val Val Thr Glu Ile Cys Leu Cys
                805                 810                 815

Ser Gln Leu Ser Lys Arg Val Gln Leu Leu Lys Lys Phe Ile Lys Ile
            820                 825                 830

Ala Ala His Cys Lys Glu Tyr Lys Asn Leu Asn Ser Phe Phe Ala Ile
        835                 840                 845

Ala Met Gly Leu Ser Asn Val Ala Val Ser Arg Leu Ala Leu Thr Trp
    850                 855                 860

Glu Lys Leu Pro Ser Lys Phe Lys Lys Phe Tyr Ala Glu Phe Glu Ser
865                 870                 875                 880

Leu Met Asp Pro Ser Arg Asn His Arg Ala Tyr Arg Leu Thr Val Ala
                885                 890                 895

Lys Leu Glu Pro Pro Val Ile Pro Phe Met Pro Leu Leu Ile Lys Ala
            900                 905                 910

His Asp Cys Lys Tyr Gly Gln Asn Ser Glu Ile Leu Gln Glu Pro Thr
        915                 920                 925

Leu Gln Ser
    930

<210> SEQ ID NO 19
<211> LENGTH: 944
<212> TYPE: PRT
<213> ORGANISM: Pongo pygmaeus

<400> SEQUENCE: 19

Pro Met Val Ala Ala His Ala Ala His Ser Ser Ser Ala Glu Trp
 1               5                  10                  15

Ile Ala Cys Leu Asp Lys Arg Pro Leu Glu Arg Ser Ser Glu Asp Val
                20                  25                  30

Asp Ile Ile Phe Thr Arg Leu Lys Glu Val Lys Ala Phe Glu Lys Phe
            35                  40                  45

His Pro Asn Leu Leu His Gln Ile Cys Leu Cys Gly Tyr Tyr Glu Asn
        50                  55                  60

Leu Glu Lys Gly Ile Thr Leu Phe Arg Gln Gly Asp Ile Gly Thr Asn
65                  70                  75                  80

Trp Tyr Ala Val Leu Ala Gly Ser Leu Asp Val Lys Val Ser Glu Thr
                85                  90                  95

Ser Ser His Gln Asp Ala Val Thr Ile Cys Thr Leu Gly Ile Gly Thr
            100                 105                 110

Ala Phe Gly Glu Ser Ile Leu Asp Asn Thr Pro Arg His Ala Thr Ile
        115                 120                 125
```

```
Val Thr Arg Glu Ser Ser Glu Leu Leu Arg Ile Glu Gln Lys Asp Phe
    130                 135                 140

Lys Ala Leu Trp Glu Lys Tyr Arg Gln Tyr Met Ala Gly Leu Leu Ala
145                 150                 155                 160

Pro Pro Tyr Gly Val Met Glu Thr Gly Ser Asn Asn Asp Arg Ile Pro
                165                 170                 175

Asp Lys Glu Asn Thr Pro Leu Ile Glu Pro His Val Pro Leu Arg Pro
                180                 185                 190

Ala Asn Thr Ile Thr Lys Val Pro Ser Glu Lys Ile Leu Arg Ala Gly
                195                 200                 205

Lys Ile Leu Arg Asn Ala Ile Leu Ser Arg Ala Pro His Met Ile Arg
210                 215                 220

Asp Arg Lys Tyr His Leu Lys Thr Tyr Arg Gln Cys Cys Val Gly Thr
225                 230                 235                 240

Glu Leu Val Asp Trp Met Met Gln Gln Thr Pro Cys Val His Ser Arg
                245                 250                 255

Thr Gln Ala Val Gly Met Trp Gln Val Leu Leu Glu Asp Gly Val Leu
                260                 265                 270

Asn His Val Asp Gln Glu His His Phe Gln Asp Lys Tyr Leu Phe Tyr
            275                 280                 285

Arg Phe Leu Asp Asp Glu Asn Glu Asp Ala Pro Leu Pro Thr Glu Glu
            290                 295                 300

Glu Lys Lys Glu Cys Asp Glu Glu Leu Gln Asp Thr Met Leu Leu Leu
305                 310                 315                 320

Ser Gln Met Gly Pro Asp Ala His Met Arg Met Ile Leu Arg Lys Pro
                325                 330                 335

Pro Gly Gln Arg Thr Val Asp Asp Leu Glu Ile Ile Tyr Glu Glu Leu
            340                 345                 350

Leu His Thr Lys Ala Leu Ser His Leu Ser Thr Thr Val Lys Arg Glu
        355                 360                 365

Leu Ala Gly Val Leu Ile Phe Glu Ser His Ala Lys Gly Gly Thr Val
    370                 375                 380

Leu Phe Asn Gln Gly Glu Glu Gly Thr Ser Trp Tyr Ile Ile Leu Lys
385                 390                 395                 400

Gly Ser Val Asn Val Val Ile Tyr Gly Lys Gly Val Val Cys Thr Leu
                405                 410                 415

His Glu Gly Asp Asp Phe Gly Lys Leu Ala Leu Val Asn Asp Ala Pro
            420                 425                 430

Arg Ala Ala Ser Ile Val Leu Arg Glu Asp Asn Cys His Phe Leu Arg
            435                 440                 445

Val Asp Lys Glu Asp Phe Asn Arg Ile Leu Arg Asp Val Glu Ala Asn
450                 455                 460

Thr Val Arg Leu Lys Glu His Asp Gln Asp Val Leu Val Leu Glu Lys
465                 470                 475                 480

Val Pro Ala Gly Asn Arg Ala Ser Asn Gln Gly Asn Ser Gln Pro Gln
                485                 490                 495

Gln Lys Tyr Thr Val Met Ser Gly Thr Pro Glu Lys Ile Leu Glu His
            500                 505                 510

Phe Leu Glu Thr Ile Arg Leu Glu Ala Thr Leu Asn Glu Ala Thr Asp
            515                 520                 525

Ser Val Leu Asn Asp Phe Ile Met Met His Cys Val Phe Met Pro Asn
530                 535                 540

Thr Gln Leu Cys Pro Ala Leu Val Ala His Tyr His Ala Gln Pro Ser
545                 550                 555                 560
```

Gln Gly Thr Glu Gln Glu Lys Met Asp Tyr Ala Leu Asn Asn Lys Arg
            565                 570                 575

Arg Val Ile Arg Leu Val Leu Gln Trp Ala Ala Met Tyr Gly Asp Pro
        580                 585                 590

Leu Gln Glu Asp Val Ser Met Ala Phe Leu Glu Glu Phe Tyr Val
        595                 600                 605

Ser Val Ser Asp Asp Ala Arg Met Ile Ala Ala Leu Lys Glu Gln Leu
        610                 615                 620

Pro Glu Leu Glu Lys Ile Val Lys Gln Ile Ser Glu Asp Ala Lys Ala
625                 630                 635                 640

Pro Gln Lys Lys His Lys Val Leu Leu Gln Gln Phe Asn Thr Gly Asp
                645                 650                 655

Glu Arg Ala Gln Lys Arg Gln Pro Ile Arg Gly Ser Asp Glu Val Leu
            660                 665                 670

Phe Lys Val Tyr Cys Met Asp His Thr Tyr Thr Ile Arg Val Pro
        675                 680                 685

Val Ala Ala Ser Val Lys Glu Val Ile Ser Ala Val Ala Asp Lys Leu
        690                 695                 700

Gly Ser Gly Glu Gly Leu Ile Val Val Lys Met Ser Ser Gly Gly Glu
705                 710                 715                 720

Lys Val Val Leu Lys Pro Asn Asp Val Ser Val Phe Thr Thr Leu Thr
                725                 730                 735

Ile Asn Gly Arg Leu Phe Ala Cys Pro Arg Glu Gln Phe Asp Ser Leu
            740                 745                 750

Thr Pro Leu Pro Glu Gln Glu Gly Pro Thr Val Gly Thr Val Gly Thr
        755                 760                 765

Phe Glu Leu Met Ser Ser Lys Asp Leu Ala Tyr Gln Met Thr Ile Tyr
        770                 775                 780

Asp Trp Glu Leu Phe Asn Cys Val His Glu Leu Glu Leu Ile Tyr His
785                 790                 795                 800

Thr Phe Gly Arg His Asn Phe Lys Lys Thr Thr Ala Asn Leu Asp Leu
                805                 810                 815

Phe Leu Arg Arg Phe Asn Glu Ile Gln Phe Trp Val Val Thr Glu Ile
            820                 825                 830

Cys Leu Cys Ser Gln Leu Ser Lys Arg Val Gln Leu Leu Lys Lys Phe
        835                 840                 845

Ile Lys Ile Ala Ala His Cys Lys Glu Tyr Lys Asn Leu Asn Ser Phe
        850                 855                 860

Phe Ala Ile Ala Met Gly Leu Ser Asn Val Ala Val Ser Arg Leu Ala
865                 870                 875                 880

Leu Thr Trp Glu Arg Met Ile Ala Asn Thr Ala Arg Thr Val Arg Tyr
                885                 890                 895

Tyr Arg Ser Gln Pro Phe Asn Pro Asp Ala Ala Gln Ala Asn Lys Asn
            900                 905                 910

His Gln Asp Val Trp Ser Tyr Val Arg Gln Leu Asn Val Ile Asp Asn
        915                 920                 925

Gln Arg Thr Leu Ser Gln Met Ser His Arg Leu Glu Pro Arg Arg Pro
        930                 935                 940

<210> SEQ ID NO 20
<211> LENGTH: 1011
<212> TYPE: PRT
<213> ORGANISM: Mus musculus

<400> SEQUENCE: 20

```
Met Val Ala Ala His Ala His Ser Gln Ser Ala Glu Trp Ile
  1               5                  10                  15
Ala Cys Leu Asp Lys Arg Pro Leu Glu Arg Ser Ser Glu Asp Val Asp
                 20                  25                  30
Ile Ile Phe Thr Arg Leu Lys Gly Val Lys Ala Phe Glu Lys Phe His
             35                  40                  45
Pro Asn Leu Leu Arg Gln Ile Cys Leu Cys Gly Tyr Tyr Glu Asn Leu
 50                  55                  60
Glu Lys Gly Ile Thr Leu Phe Arg Gln Gly Asp Ile Gly Thr Asn Trp
 65                  70                  75                  80
Tyr Ala Val Leu Ala Gly Ser Leu Asp Val Lys Val Ser Glu Thr Ser
                 85                  90                  95
Ser His Gln Asp Ala Val Thr Ile Cys Thr Leu Gly Ile Gly Thr Ala
                100                 105                 110
Phe Gly Glu Ser Ile Leu Asp Asn Thr Pro Arg His Ala Thr Ile Val
            115                 120                 125
Thr Arg Glu Ser Ser Glu Leu Leu Arg Ile Glu Gln Glu Asp Phe Lys
130                 135                 140
Ala Leu Trp Glu Lys Tyr Arg Gln Tyr Met Ala Gly Leu Leu Ala Pro
145                 150                 155                 160
Pro Tyr Gly Val Met Glu Thr Gly Ser Asn Asn Asp Arg Ile Pro Asp
                165                 170                 175
Lys Glu Asn Thr Pro Leu Ile Glu Pro His Val Pro Leu Arg Pro Ala
                180                 185                 190
His Thr Ile Thr Lys Val Pro Ser Glu Lys Ile Leu Arg Ala Gly Lys
            195                 200                 205
Ile Leu Arg Ile Ala Ile Leu Ser Arg Ala Pro His Met Ile Arg Asp
210                 215                 220
Arg Lys Tyr His Leu Lys Thr Tyr Arg Gln Cys Cys Val Gly Thr Glu
225                 230                 235                 240
Leu Val Asp Trp Met Ile Gln Gln Thr Ser Cys Val His Ser Arg Thr
                245                 250                 255
Gln Ala Val Gly Met Trp Gln Val Leu Leu Glu Asp Gly Val Leu Asn
                260                 265                 270
His Val Asp Gln Glu Arg His Phe Gln Asp Lys Tyr Leu Phe Tyr Arg
            275                 280                 285
Phe Leu Asp Asp Glu Arg Glu Asp Ala Pro Leu Pro Thr Glu Glu Glu
290                 295                 300
Lys Lys Glu Cys Asp Glu Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Asp Glu Leu Leu
                340                 345                 350
His Ile Lys Ala Leu Ser His Leu Ser Thr Thr Val Lys Arg Glu Leu
            355                 360                 365
Ala Gly Val Leu Ile Phe Glu Ser His Ala Lys Gly Gly Thr Val Leu
370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
```

```
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
            435                 440                 445
Asp Lys Glu Asp Phe Asn Arg Ile Leu Arg Asp Val Glu Ala Asn Thr
450                 455                 460
Val Arg Leu Lys Glu His Asp Gln Asp Val Leu Val Leu Glu Lys Val
465                 470                 475                 480
Pro Ala Gly Asn Arg Ala Ala Asn Gln Gly Asn Ser Gln Pro Gln Gln
                485                 490                 495
Lys Tyr Thr Val Met Ser Gly Thr Pro Glu Lys Ile Leu Glu His Phe
            500                 505                 510
Leu Glu Thr Ile Arg Leu Glu Pro Ser Leu Asn Glu Ala Thr Asp Ser
            515                 520                 525
Val Leu Asn Asp Phe Val Met Met His Cys Val Phe Met Pro Asn Thr
            530                 535                 540
Gln Leu Cys Pro Ala Leu Val Ala His Tyr His Ala Gln Pro Ser Gln
545                 550                 555                 560
Gly Thr Glu Gln Glu Arg Met Asp Tyr Ala Leu Asn Asn Lys Arg Arg
                565                 570                 575
Val Ile Arg Leu Val Leu Gln Trp Ala Ala Met Tyr Gly Asp Leu Leu
            580                 585                 590
Gln Glu Asp Asp Val Ala Met Ala Phe Leu Glu Glu Phe Tyr Val Ser
            595                 600                 605
Val Ser Asp Asp Ala Arg Met Met Ala Ala Phe Lys Glu Gln Leu Pro
610                 615                 620
Glu Leu Glu Lys Ile Val Lys Gln Ile Ser Glu Asp Ala Lys Ala Pro
625                 630                 635                 640
Gln Lys His Lys Val Leu Leu Gln Gln Phe Asn Thr Gly Asp Glu
                645                 650                 655
Arg Ala Gln Lys Arg Gln Pro Ile Arg Gly Ser Asp Glu Val Leu Phe
                660                 665                 670
Lys Val Tyr Cys Ile Asp His Thr Tyr Thr Thr Ile Arg Val Pro Val
            675                 680                 685
Ala Ala Ser Val Lys Glu Val Ile Ser Ala Val Ala Asp Lys Leu Gly
            690                 695                 700
Ser Gly Glu Gly Leu Ile Ile Val Lys Met Asn Ser Gly Gly Glu Lys
705                 710                 715                 720
Val Val Leu Lys Ser Asn Asp Val Ser Val Phe Thr Thr Leu Thr Ile
                725                 730                 735
Asn Gly Arg Leu Phe Ala Cys Pro Arg Glu Gln Phe Asp Ser Leu Thr
            740                 745                 750
Pro Leu Pro Glu Gln Glu Gly Pro Thr Thr Gly Thr Val Gly Thr Phe
            755                 760                 765
Glu Leu Met Ser Ser Lys Asp Leu Ala Tyr Gln Met Thr Thr Tyr Asp
            770                 775                 780
Trp Glu Leu Phe Asn Cys Val His Glu Leu Glu Leu Ile Tyr His Thr
785                 790                 795                 800
Phe Gly Arg His Asn Phe Lys Lys Thr Thr Ala Asn Leu Asp Leu Phe
                805                 810                 815
Leu Arg Arg Phe Asn Glu Ile Gln Phe Trp Val Val Thr Glu Val Cys
            820                 825                 830
Leu Cys Ser Gln Leu Ser Lys Arg Val Gln Leu Leu Lys Lys Phe Ile
            835                 840                 845
```

```
Lys Ile Ala Ala His Cys Lys Glu Tyr Lys Asn Leu Asn Ser Phe Phe
850                 855                 860

Ala Ile Val Met Gly Leu Ser Asn Val Ala Val Ser Arg Leu Ala Leu
865                 870                 875                 880

Thr Trp Glu Lys Leu Pro Ser Lys Phe Lys Lys Phe Tyr Ala Glu Phe
                885                 890                 895

Glu Ser Leu Met Asp Pro Ser Arg Asn His Arg Ala Tyr Arg Leu Thr
                900                 905                 910

Ala Ala Lys Leu Glu Pro Pro Leu Ile Pro Phe Met Pro Leu Leu Ile
                915                 920                 925

Lys Asp Met Thr Phe Thr His Glu Gly Asn Lys Thr Phe Ile Asp Asn
                930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
                965                 970                 975

Asn Lys Asn His Gln Asp Val Arg Ser Tyr Val Arg Gln Leu Asn Val
                980                 985                 990

Ile Asp Asn Gln Arg Thr Leu Ser Gln Met Ser His Arg Leu Glu Pro
                995                 1000                1005

Arg Arg Pro
    1010

<210> SEQ ID NO 21
<211> LENGTH: 3036
<212> TYPE: DNA
<213> ORGANISM: Mus musculus

<400> SEQUENCE: 21
atggtcgctg cgcacgctgc acactctcag tcctcggccg agtggatcgc ctgcctggat    60
aaaaggccgt tggagcgatc tagtgaagat gtggacataa ttttcacgcg gctgaaagga    120
gttaaagctt ttgagaaatt tcacccaaac ctccttcgtc agatttgttt atgcggttac    180
tatgagaacc tggaaaaagg aatcacactg tttcgccaag gggatattgg aaccaactgg    240
tatgctgtcc tggctgggtc tttggatgtt aaagtgtctg agaccagcag tcaccaggat    300
gcggtgacca tctgcactct gggaattggg acagcctttg agagtccatc tctggataac    360 accccctcgcc atgcaaccat cgttaccagg gagagcagcg aacttctccg cattgagcag    420
gaggacttca aggcactatg ggagaaatac cgacagtata tggccggact ctctggctcct    480 ccctatggtg ttatggaaac gggctctaac aatgacagga ttcctgacaa ggagaataca    540
cctctcattg aaccccacgt tcctctccgt cctgctcaca ccattaccaa ggtcccttca    600
gagaagatcc tcagagctgg aaaaatttta cgaattgcca ttctctctcg agctccccac    660
atgataagag acagaaagta ccacctaaag acatacagac aatgctgtgt tgggactgag    720
ctggtagact ggatgataca gcagacatcc tgtgttcact cgcggactca agctgttggc    780
atgtggcaag tcttgctgga agatggtgtc ctcaaccatg tggaccagga gcgccatttc    840
caagacaaat atttatttta tcgatttctg gatgacgagc gtgaggatgc ccctttgcct    900
actgaggaag agaagaagga gtgtgatgaa gaacttcagg acaccatgct gctgctctca    960 cagatggggcc ctgacgccca catgagaatg atcctgcgaa aaccacctgg ccagaggact    1020
gtggatgacc tagagattat ctacgacgag ctccttcata ttaaagcctt atcccatctc    1080 tctctaccacag tgaaacggga gttagcaggt gttctcattt ttgagtctca cgccaaagga    1140
ggaactgtgt tgtttaacca ggggaagaa ggtacctcct ggtacatcat tctgaaagga    1200
```

```
tccgtgaatg tagtcattta tggcaagggt gtggtctgca ccctgcacga aggagatgac    1260
tttggcaagt tagctctagt gaacgatgct ccaagagctg cctccattgt tcttcgggaa    1320
gataattgtc acttcctaag agtcgacaag gaagacttca atcggattct gagggacgtt    1380
gaggcgaata cagtcagact taaagaacat gaccaagatg tcttggtact ggagaaggtc    1440
ccagcaggga acagagctgc taatcaagga aactcacagc ctcagcaaaa gtatactgtg    1500
atgtcaggaa cacctgaaaa gattttagag cattttctag aaacaatacg ccttgagcca    1560
tcgttgaatg aagcaacaga ttcggtttta aatgactttg ttatgatgca ctgtgttttt    1620
atgccaaata cccagctttg ccctgcccct gtggcccatt accacgcaca gccttctcaa    1680
ggtaccgagc aggagagaat ggattatgcc ctcaacaaca agaggcgggt catccgcttg    1740
gtcctgcagt gggcggccat gtatggcgat ctcctccaag aagatgatgt ggccatggcc    1800
ttcctggagg agttctatgt gtctgtatca gatgacgcac ggatgatggc tgccttcaag    1860
gagcagctgc cagagctgga gaagattgtc aagcaaatct cagaagacgc aaaagctcca    1920
cagaagaagc acaaggtgct tttgcaacag ttcaacacag gtgacgagag ggcccagaag    1980
cgtcagccta ttcgtggctc tgatgaggtt ttgttcaagg tctactgcat cgaccacacc    2040
tatactacca ttcgtgtgcc ggtagctgcc tcggtgaagg aagtcatcag tgcagtagct    2100
gacaaactgg gctcagggga aggcctgatc atcgtcaaga tgaactctgg aggagaaaag    2160
gtggtgctga aatctaatga tgtttcagta tttacgacgc tcaccattaa tggacgcctg    2220
tttgcctgcc cgagagagca attcgactca ctgactccct tgccggaaca ggaaggcccg    2280
accactggga cagtgggaac atttgagctg atgagctcga aagacctggc gtaccagatg    2340
acaacctacg attgggaact cttcaactgt gtgcatgagc tggagctaat ctaccacaca    2400
tttggaaggc ataattttaa aaagaccacg gcaaacttgg atttgttcct gaggaggttt    2460
aatgaaattc agttttgggt tgtcactgag gtctgccttt gttcccagct cagcaaacgt    2520
gttcagcttt tgaaaaaatt tatcaagata gcggctcact gcaaggagta caaaaatcta    2580
aattcctttt tcgccatcgt catgggactc agcaacgtgg ccgtgagccg cttggcacta    2640
acgtgggaga aactgccgag caagtttaag aagttctatg cggagtttga gagcttgatg    2700
gatccttcca gaaaccacag ggcatacagg ctgacagcag ccaagctgga gcccctctc    2760
atccctttca tgcccttgct tattaaagat atgacatttα ctcatgaggg gaacaagacg    2820
ttcattgaca atctagtaaa ctttgaaaaa atgcgcatga ttgcaaacac tgccagaaca    2880
gtacggtact acaggagcca gcccttcaat ccggatgccg ctcaagctaa taagaaccat    2940
caggatgtcc ggagttatgt acggcaatta aatgtgattg acaaccagag aactttatca    3000
cagatgtcac acagattaga gcctcgaagg ccatag                             3036
```

US 8,236,523 B2

CAMP REPORTERS AND HIGH THROUGHPUT ASSAYS

This application claims the benefit of and is a continuation-in-part of PCT/US2005/030099 filed Aug. 23, 2005, which claims the benefit of provisional applications Ser. No. 60/603,623 filed Aug. 23, 2004 and Ser. No. 60/681,923 filed May 17, 2005. This application also claims the benefit of Ser. No. 60/730,583 filed Oct. 27, 2005. Each of these applications is incorporated by reference in its entirety herein.

This invention was made using funds from NIH grants DK073368, GM066170 and GM08763 and USPHS training grant T32 CA009243. The government retains certain rights in the invention.

FIELD OF THE INVENTION

The invention relates to detection of cAMP levels.

BACKGROUND OF THE INVENTION

Spatial and temporal control of cAMP signaling is crucial to differential regulation of cellular targets involved in various signaling cascades. Various methods exist for detecting and measuring intracellular cAMP, but none are ideally suited for monitoring spatial and temporal distributions of cAMP in living cells. For example, radioimmunoassay or enzyme immunoassays for measuring cAMP require destroying large amounts of cells or tissue, have very poor spatial and temporal resolution, and measure total rather than free cAMP. Use of engineered cyclic nucleotide-gated channels to detect free cAMP provides good temporal resolution and quantification but uses indirect calcium measurements or nontrivial patch-clamp techniques and lacks the flexibility of measuring cAMP changes within various subcellular compartments (Rich et al., Proc. Natl. Acad. Sci. USA 98, 13049-54, 2001; Rich et al., J. Gen. Physiol. 116, 147-61, 2000). Free cAMP can be imaged in single cells microinjected with fluorophore-labeled C and R subunits (Adams et al., Nature 349, 694-97, 1991) or in cells expressing two colors of GFP mutants fused to the C and R subunits (Zaccolo et al., Nat. Cell Biol. 2, 25-29, 2000), which dissociate from each other and lose fluorescence resonance energy transfer upon elevation of cAMP. However, the expression levels of the two fusions have to be carefully matched to allow reliable measurement. Even so, mixed tetramerization may occur between the fluorophore-attached subunits and endogenous partners, reducing the number of functional reporter molecules. Furthermore, it can be difficult to target such bimolecular reporters to different subcellular locations while maintaining appropriate stoichiometry.

There is a need in the art for sensitive cAMP reporters and methods which can be used for accurate measurements of spatial and temporal cAMP distributions in living cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A, FRET response of HEK-293 cells transfected with ICUE1. The first image is a YFP-only image. Pseudocolor images depict the FRET response of the reporter to isoproterenol (ISO) stimulation at various time points. Scale bar represents 10 µm. FIG. 2B, Representative emission ratio time courses of ICUE1 and the R522E mutant stimulated with 10 µM ISO followed by 10 µM propranolol and 50 µM forskolin (FSK). FIG. 2C, Representative emission ratio time courses of ICUE1 stimulated with 10 µM ISO, 50 µM FSK, 10 µM $PGE_1$, 300 µM 8-pCPT-2'-O-Me-cAMP, or 100 µM of DMNB-cAMP followed by UV uncaging. The flash signs indicate 5 second UV flash at two different time points.

FIG. 3A, Domain structures of the fusion constructs. FIG. 3B, YFP-only images showing plasma membrane and nuclear distributions of various fusions. Scale bars represent 10 µm. Merged pseudocolor images showing co-localization of nuclear localized ICUE1 with Hoechst 33342 cell-permeable dye in nucleus and mitochondria-targeted ICUE1 with MitoTracker at mitochondria. FIG. 3C, Representative emission ratio time courses for untagged (ICUE1), plasma membrane-targeted (pm ICUE1), mitochondria-targeted (MitoCOX- and MitoDAKAP1-ICUE1 ) and nuclear-localized cAMP reporters (NLS-ICUE1) stimulated with ISO (10 µM). FIG. 3D, Representative emission ratio time courses for pm ICUE1 stimulated with $PGE_1$ (10 µM), followed by the removal of $PGE_1$ and the addition of ISO (10 µM). FIG. 3E, Representative emission ratio time courses for NLS-ICUE1 in response to $PGE_1$ (10 µM) and ISO (10 µM) separated by a washing step.

FIG. 4A, Cellular distribution of different fusions. FIG. 4B, Representative emission ratio time courses for the pm ICUE1 and nuclear localized PKA activity reporter (NLS-AKAR) in the same cell stimulated with ISO (10 µM). Identical results were found in four different cells. The AKAR response was plotted using normalized ratio of yellow to cyan emissions. FIG. 4C, Representative emission ratio time courses for pm ICUE1 and NLS-ICUE1 in the same cell stimulated with 10 µM ISO followed by 10 µM propranolol (n=4).

FIG. 10A, domain structures of the second generation of the "Indicator of cAMP Using Epac," ICUE2, as well as its Venus and cpVenus (cpV) variants. ICUE cpV L194 (R373E) contains an R373E mutation in the cAMP binding site. FIG. 10B, representative time courses of HEK-293 cells expressing ICUE cpV L194 (ICUE3, circles), ICUE2 (squares), and ICUE (R373E) (triangles), treated with 50 µM FSK.

FIG. 13A, normalized emission ratio (cyan/yellow) from cells expressing ICUE treated with individual library compounds, compared to the negative control in which only buffer was added and the positive control in which isoproterenol (ISO) (250 nM) and 3-Isobutyl-1-methylxanthine (IBMX)(100 µM) was added (agonist screen). FIG. 13B, normalized emission ratio (cyan/yellow) from cells expressing ICUE first treated with individual library compounds for about 15 min then stimulated by ISO (250 nM) and IBMX (100 µM) (antagonist screen). The positive control in which only ISO and IBMX was added and the negative control in which only buffer was added are shown as labeled.

DETAILED DESCRIPTION OF THE INVENTION

Figure 1:
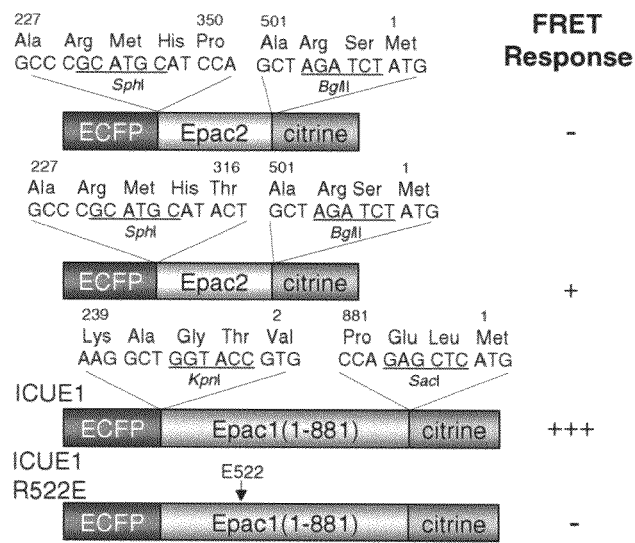
FIG. 1. Domain structure and comparison of FRET responses for cAMP reporters. Sandwiched between enhanced CFP (ECFP) and citrine are truncated forms of Epac2 or full length Epac1 (with or without an R522E mutation). The construct comprising full-length Epac1 generated the biggest FRET response and was designated as ICUE1.

The invention provides highly sensitive reporter molecules by which temporal and spatial distribution of cAMP can be determined in living tissues. "cAMP reporters" (also referred to as "reporters") of the invention comprise (a) a donor moiety; (b) a polypeptide linked to the donor moiety and comprising a cAMP-binding domain of an "exchange protein directly activated by cAMP" (Epac) or a cAMP-binding domain (including mutated versions) from protein kinase A, a cyclic nucleotide-gated channel, or other cAMP-responsive domain or protein (e.g., the Tandem GAF Domain of phosphodiesterases; Gross-Langenhoff et al., *J. Biol. Chem.* 282, 2841-46); and (c) an acceptor moiety linked to the polypeptide. In the absence of cAMP, the donor moiety and the acceptor moiety are in sufficient proximity to each other to exhibit a detectable resonance energy transfer when the donor is excited. Binding of cAMP to the cAMP-binding domain causes a conformational change which changes the distance or relative orientation between the donor and acceptor moieties and alters the resonance energy transfer between the moieties. The degree of alteration reflects cAMP levels and can be detected qualitatively or quantitatively.

cAMP reporters of the invention are useful for detecting intracellular cAMP and for assessing intracellular cAMP dynamics, although they also can be used in in vitro assays. Nucleic acid molecules encoding cAMP reporters of the invention can be delivered to cells using standard DNA transfection techniques, thereby generating cells which express high levels of the reporters. The reporters have advantages over previous methods for assessing cAMP dynamics inside cells. The reporters are unimolecular and can be readily targeted to different subcellular locations or fused to signaling components. They can be used to examine compartmentalized Epac activities and their physiological functions. For example, as described in the Examples below, a cAMP reporter targeted to plasma membrane, mitochondria, or nucleus revealed differential dynamics of cAMP signaling in response to the activation of the β-adrenergic receptor (β-AR) or the prostanoid receptor.

cAMP reporters of the invention permit simultaneous imaging of cAMP dynamics and PKA phosphorylation in single living cells using locus-specific reporters. Methods of the invention take advantage of spatial separation of subcellular events and provide unambiguous temporal correlation of these events. This methodology complements multi-color imaging (Violin et al., *J. Cell Biol.* 161, 899-909, 2003; DeBernardi & Brooker, *Proc. Natl. Acad. Sci. USA* 93, 4577-82, 1996) and is well suited for simultaneous monitoring of multiple signaling events and for evaluating the information flow within signaling cascades or crosstalk between different pathways (Zaccolo, *Cir. Res.* 94, 866-73, 2004).

Polypeptides

Polypeptides used in cAMP reporters of the invention comprise a cAMP-binding domain of an Epac, e.g., Epac1 or Epac2. Epac1 and Epac2 are well-characterized, and the locations of their cAMP-binding domains are known. See de Rooij et al., *J. Biol. Chem.* 275, 20829-36, 2000. Useful polypeptides include full-length, truncated, and mutated Epac1 or Epac2 from any species which has an Epac, such as rodents (e.g., mice, rats) and primates (e.g., humans, orangutans). The amino acid sequences of several Epac1 and Epac2 proteins are provided in SEQ ID NOS:1, 3, and 17-20. Nucleic acid sequences which encode SEQ ID NOS:1, 3, and 20 are shown in SEQ ID NOS:2, 4, and 21, respectively. The cAMP-binding domain in a cAMP reporter typically can bind cAMP; however, polypeptides comprising non-functional cAMP-binding domains are also useful, for example, for use in control reporters. The polypeptide itself preferably does not substantially emit light or transfer energy to excite the acceptor moiety.

Donor and Acceptor Moieties

As used here, a "donor moiety" is a fluorophore or a luminescent moiety. The absorption spectrum of the "acceptor moiety" overlaps the emission spectrum of the donor moiety. The acceptor moiety does not need to be fluorescent and can be a fluorophore, chromophore, or quencher. In some embodiments both the donor and acceptor moieties are fluorescent proteins. In other embodiments both the donor and acceptor moieties are luminescent moieties. In yet other embodiments, either one of the donor or acceptor moieties can be a fluorescent protein while the other moiety is a luminescent moiety. In other embodiments, the acceptor moiety is a "quencher moiety."

When both the donor and acceptor moieties are fluorophores, resonance energy transfer is detected as "fluorescence resonance energy transfer" (FRET). If a luminescent moiety is involved, resonance energy transfer is detected as "luminescent resonance energy transfer" (LRET). LRET includes "bioluminescent resonance energy transfer" (BRET; Boute et al., *Trends Pharmacol. Sci.* 23, 351-54, 2002; Ayoub et al., *J. Biol. Chem.* 277, 21522-28, 2002). Because excitation of the donor moiety does not require exogenous illumination in an LRET method, such methods are particularly useful in live tissue and animal imaging, because penetration of the excitation light is no longer a concern. LRET methods have a high contrast and high signal-to-noise ratio; 2) no photobleaching occurs; and 3) quantification is simplified because the acceptor moiety is not directly excited.

Suitable acceptor moieties include, for example, a coumarin, a xanthene, a fluorescein, a fluorescent protein, a circularly permuted fluorescent protein, a rhodol, a rhodamine, a resorufin, a cyanine, a difluoroboradiazaindacene, a phthalocyanine, an indigo, a benzoquinone, an anthraquinone, an azo compound, a nitro compound, an indoaniline, a diphenylmethane, a triphenylmethane, and a zwitterionic azopyridinium compound.

Suitable donor moieties include, but are not limited to, a coumarin, a xanthene, a rhodol, a rhodamine, a resorufin, a cyanine dye, a bimane, an acridine, an isoindole, a dansyl dye, an aminophthalic hydrazide, an aminophthalimide, an aminonaphthalimide, an aminobenzofuran, an aminoquinoline, a dicyanohydroquinone, a semiconductor fluorescent nanocrystal, a fluorescent protein, a circularly permuted fluorescent protein, and fluorescent lanthanide chelate.

Fluorescent Proteins

In some preferred embodiments either or both of the donor and acceptor moieties is a fluorescent protein. Suitable fluorescent proteins include green fluorescent proteins (GFP), red fluorescent proteins (RFP), yellow fluorescent proteins (YFP), and cyan fluorescent proteins (CFP). Useful fluorescent proteins also include mutants and spectral variants of these proteins which retain the ability to fluoresce.

RFPs include Discosoma RFPs, such Discosoma DsRed (SEQ ID NO:9) or a mutant thereof which includes an Ile125Arg mutation, or a non-oligomerizing tandem DsRed containing, for example, two RFP monomers linked by a peptide linker. For example, a non-oligomerizing tandem RFP can contain two DsRed monomers or two mutant DsRed-I125R monomers linked by a peptide (having, for example, the amino acid sequence shown in SEQ ID NO:10).

Useful GFPs include an *Aequorea* GFP (e.g., SEQ ID NO:11), a *Renilla* GFP, a *Phialidium* GFP, and related fluorescent proteins for example, a cyan fluorescent protein (CFP), a yellow fluorescent protein (YFP), or a spectral variant of the CFP or YFP. CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. Spectral variants include an enhanced GFP (EGFP; SEQ ID NO:12), an enhanced CFP (ECFP; SEQ ID NO:13), an enhanced YFP (EYFP; SEQ ID NO:14), and an EYFP with V68L and Q69K mutations. Other examples of fluorescent proteins comprising mutations are *Aequorea* GFP with one or more mutations at amino acid residues A206, L221 or F223 of SEQ ID NO:11 (e.g., mutations A206K, L221K, F223R, Q80R); mutations L221K and F223R of ECFP (SEQ ID NO:12), and EYFP-V68L/Q69K of SEQ ID NO:11. See also US 2004/0180378; U.S. Pat. Nos. 6,150,176; 6,124,128; 6,077,707; 6,066,476; 5,998,204; and 5,777,079; Chalfie et al., *Science* 263:802-805, 1994.

Other useful GFP-related fluorescent proteins include those having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:11, include the substitutions F64L, V68L, S72A, T44A, F99S, Y145F, N146I, M153T, M153A, V163A, I167T, S175G, S205T, and N212K.

Luminescent Moieties

Luminescent moieties useful in a cAMP reporter include lanthanides, which can be in the form of a chelate, including a lanthanide complex containing the chelate (e.g, β-diketone chelates of cerium, praseodymium, neodymium, promethium, samarium, europium, gadolinium, terbium, dysprosium, holmium, erbium, thulium, or ytterbium). Lanthanide chelates are well known in the art. See Soini and Kojola, *Clin. Chem.* 29, 65, 1983; Hemmila et al., *Anal. Biochem.* 137, 335 1984; Lovgren et al., In: Collins & Hoh, eds., *Alternative Immunoassays*, Wiley, Chichester, U.K., p. 203, 1985; Hemmila, *Scand. J. Clin. Lab. Invest.* 48, 389, 1988; Mikola et al., *Bioconjugate Chem.* 6, 235, 1995; Peruski et al., *J. Immunol. Methods* 263, 35-41, 2002; U.S. Pat. Nos. 4,374,120; and 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). See also US 20040146895.

Luminescent proteins include, but are not limited to, lux proteins (e.g., luxCDABE from *Vibrio fischerii*), luciferase proteins (e.g., firefly luciferase, *Gaussia* luciferase, *Pleuromamma* luciferase, and luciferase proteins of other beetles, Dinoflagellates (*Gonylaulax; Pyrocystis*;), Annelids (*Dipocardia*), Molluscs (*Lativa*), and Crustacea (*Vargula; Cypridina*), and green fluorescent proteins of bioluminescent coelenterates (e.g., *Aequorea Victoria, Renilla mullerei, Renilla reniformis*; see Prendergast et al., *Biochemistry* 17, 3448-53, 1978; Ward et al., *Photochem. Photobiol.* 27, 389-96, 1978; Ward et al., *J. Biol. Chem.* 254, 781-88, 1979; Ward et al., *Photochem. Photobiol. Rev* 4, 1-57, 1979; Ward et al., *Biochemistry* 21, 4535-40, 1982). Many of these proteins are commercially available. Firefly luciferase is available from Sigma, St. Louis, Mo., and Boehringer Mannheim Biochemicals, Indianapolis, Ind. Recombinantly produced firefly luciferase is available from Promega Corporation, Madison, Wis. Jellyfish aequorin and luciferase from *Renilla* are commercially available from Sealite Sciences, Bogart, Ga.

The DNA sequences of the aequorin and other luciferases employed for preparation of some cAMP reporters of the invention can be derived from a variety of sources. For example, cDNA can be prepared from mRNA isolated from the species disclosed above. See Faust, et al., *Biochem.* 18, 1106-19, 1979; De Wet et al., *Proc. Natl. Acad. Sci. USA* 82, 7870-73, 1985.

Luciferase substrates (luciferins) are well known and include coelenterazine (available from Molecular Probes, Eugene, Oreg.) and ENDUREN™. These cell-permeable reagents can be directly administered to cells, as is known in the art. Luciferin compounds can be prepared according to the methods disclosed by Hori et al., *Biochemistry* 14, 2371-76, 1975; Hori et al., *Proc. Natl. Acad. Sci. USA* 74, 4285-87, 1977).

Dark Quenchers

In some embodiments the acceptor moiety is a quencher moiety, preferably a "dark quencher" (or "black hole quencher") as is known in the art. In this case, the change in conformation which occurs upon cAMP binding eliminates quenching, resulting in an increase in energy emission from the donor moiety. "Dark quenchers" themselves do not emit photons. Use of a "dark quencher" reduces or eliminates background fluorescence or luminescence which would otherwise occur as a result of energy transfer from the donor moiety. Suitable quencher moieties include dabcyl (4-(4'-dimethylaminophenylazo)-benzoic acid), QSY™-7 carboxylic acid, succinimidyl ester (N,N'-dimethyl-N,N'-diphenyl-4-((5-t-butoxycarbonylaminopentyl)aminocarbon yl) piperidinylsulfone-rhodamine (a diarylrhodamine derivative from Molecular Probes, Eugene, Oreg.). Suitable quencher moieties are disclosed, for example, in US 2005/0118619; US 20050112673; and US 20040146959.

Any suitable fluorophore may be used as the donor moiety provided its spectral properties are favorable for use with the chosen dark quencher. The donor moiety can be, for example, a Cy-dye, Texas Red, a Bodipy dye, or an Alexa dye. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, a fluorescein (e.g., fluorescein, tetrachlorofluorescein, hexachlorofluorescein), rhodamine, tetramethylrhodamine, or other like compound. Suitable fluorescent moieties for use with dark quenchers include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS).

Other suitable fluorescent moieties include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethy-loxacarbocyanine (CyA); 1H,5H,1H,15H-Xantheno[2,3,4-ij:5,6,7-i'j']diquinol-izin-18-ium, 9-[2(or 4)-[[[6-[2,5-dioxo-1-pyrrolidinyl)oxy]-6-oxohexyl]amino] sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like.

Subcellular Targeting Sequences cAMP reporters of the invention optionally can include a subcellular targeting sequence which can target a cAMP reporter to a subcellular domain such as a plasma membrane, a nuclear membrane, a cytosol, an endoplasmic reticulum, a mitochondria, a mitochondrial matrix, a chloroplast, a medial trans-Golgi cisternae, a lumen of a lysosome, or a lumen of an endosome. Many such targeting sequences are known in the art. Examples include the plasma membrane targeting sequence shown in SEQ ID NO:6, the nuclear localization signal sequence shown in SEQ ID NO:5, the mitochondrial localization sequence shown in SEQ ID NO:7, and the mitochondrial matrix targeting signal shown in SEQ ID NO:8. Targeting sequences can be linked to cAMP reporters using, for example, a tetracysteine motif such as Cys Cys Xaa Xaa Cys Cys (SEQ ID NO:15). Targeting sequences can be linked at either the N- or C-terminus of a cAMP reporter or at intermediate points in the reporter.

In some embodiments, cAMP reporters of the invention do not include those which consist of YFP which is not circularly permuted, CFP which is not circularly permuted, and any of the following polypeptides: amino acids 1-443 of SEQ ID NO:3 (a mouse Epac2), amino acids 1-149 of SEQ ID NO:3, amino acids 29-149 of SEQ ID NO:3, amino acids 285-443 of SEQ ID NO:3, amino acids 304-443 of SEQ ID NO:3, amino acids 310-443 of SEQ ID NO:3, amino acids 285-454 of SEQ ID NO:3, amino acids 285-460 of SEQ ID NO:3, and amino acids 157-316 of SEQ ID NO:1 (human Epac1).

Assembly of cAMP Reporters cAMP reporters which are fusion proteins preferably can be expressed recombinantly, and the invention provides nucleic acid molecules for this purpose. A nucleic acid molecule encoding a cAMP reporter can comprise any nucleotide sequence which encodes the amino acid sequence of the reporter. Nucleic acid molecules of the invention include single- and double-stranded DNA (including cDNA) and mRNA. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

In some embodiments the nucleic acid molecules are expression constructs which contain the necessary elements for the transcription and translation of an inserted coding sequence encoding a cAMP reporter. Expression constructs can be used as vectors for introducing cAMP reporters into cells. Methods which are well known to those skilled in the art can be used to construct expression vectors containing sequences encoding cAMP reporters and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

Expression vectors of the invention can be expressed in a variety of host cells. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems, particularly mammalian systems, including human systems. See WO 01/98340, which is incorporated herein by reference in its entirety. The choice of vector components and appropriate host cells is well within the capabilities of those skilled in the art.

Alternatively, protein or non-protein donor and/or acceptor moieties can be linked to the polypeptide by covalent attachment. There are a variety of methods known in the art which are useful for this purpose. For example, the attachment can be direct, via a functional group on the polypeptide (e.g., amino, carboxyl and sulfhydryl groups) and a reactive group on the fluorophore. Free amino groups in the polypeptide can be reacted with fluorophores derivatized with isothiocyanate, maleic anhydride, N-hydroxysuccinimide, tetrafluorylphenyl and pentafluoryl esters. Free carboxyl groups in the polypeptide can be reacted with carbodiimides such as 1-ethyl-3-[dimethylaminopropyl]carbodiimide hydrochloride to create a reactive moiety that will react with an amine moiety on the donor or acceptor moiety. Sulfhydryl groups can be attached to donor or acceptor moieties modified with maleimide and iodoacetyl groups, although such linkages are more susceptible to reduction than linkages involving free amino groups. The polypeptide can also be linked indirectly via an intermediate linker or spacer group, using chemical groups such as those listed above.

It is also possible to produce cAMP reporters of the invention using chemical methods to synthesize the amino acid sequence of the polypeptide and, optionally, one or more fluorescent or luminescent proteins. Methods include direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of polypeptide portions of cAMP reporters can be separately synthesized and combined using chemical methods to produce a full-length reporter molecule. See WO 01/98340.

Delivery of cAMP Reporters to Cells

All cAMP reporters of the invention can be introduced into cells in vitro using reversible permeabilization techniques. See U.S. Pat. Nos. 6,127,177; 6,902,931; Russo et al., *Nature Biotechnology* 15, 278-82, March 1997; Santangelo et al., *Nucleic Acids Res.* 32, 1-9, Apr. 14, 2004.

If the cAMP reporter is a fusion protein, expression vectors comprising a cAMP reporter-encoding nucleotide sequence can be transfected into any cell in vitro in which it is desired to monitor cAMP levels or distribution. Any transfection method known in the art can be used, including, for example, including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Useful vectors and methods of delivering the vectors to cells in vivo are disclosed, for example, in U.S. Pat. Nos. 6,825,012; 6,878,549; 6,645,942; 6,692,737; 6,689,758; 6,669,935; and 6,821,957.

Methods of Detecting cAMP

The invention provides various methods for detecting cAMP by detecting conformational changes in a cAMP reporter. Broadly, the methods involve detecting a change in resonance energy transfer of a cAMP reporter of the invention when the reporter is subjected to a change in cAMP concentration. cAMP binding to the reporter induces a conformational change that changes resonance energy transfer from the donor moiety to the acceptor moiety.

A change in resonance energy transfer can readily be detected using methods well known in the art. See, e.g., US 2005/0118619; US 2002/0137115; US 2003/0165920; US 2003/0186229; US 2004/0137479; US 2005/0026234; US 2005/0054573; US 2005/0118619; U.S. Pat. Nos. 6,773,885; 6,803,201; 6,818,420;

Ayoub et al., 2002; Boute et al., 2002; Domin et al., *Prog. Biomed. Optics and Imaging, Proc. SPIE*, vol 5139, 2003, pp 238-242; Evellin et al., *Methods Mol. biol.* 284, 259-70, 2004; Honda et al., *Proc. Natl. Acad. Sci. USA* 98, 437-42, Feb. 27, 2001; Honda et al., *Methods Mol. Biol.* 3, 27-44, 1005; Mongillo et al., *Cir. Res.* 95, 67-75, Jul. 9, 2004; Mongillo et al., *Methods Mol Biol.* 307, 1-14, 2005; Nagai et al., *Proc. Natl. Acad. Sci. USA* 101, 10554-59, Jul. 20, 2004; Nikolaev et al., *J. Biol. Chem.* 279, 37215-18, 2004; Polit et al., *Eur. J. Biochem.* 270, 1413-23, 2003; Ponsioen et al., *EMBO Rep.* 5, 1176-80, 2004; Santangelo et al., *Nucl. Acids Res.* 32, 1-9, e-published Apr. 14, 2004; and Warrier et al., *Am. J. Physiol. Cell Phiol.* 289, C455-61, August 2005. Properties which can be detected as resonance energy transfer (RET) measurements include a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength. Fluorescence activated cell sorting (FACS) also can be used (see below).

cAMP reporters of the invention can be used in cell-free systems, in isolated cells (for example, in primary cell culture or a cell line) or in cells in situ (e.g., in an isolated tissue sample, an isolated whole organ, or in a mammal). Subcellular distribution of cAMP or changes in cAMP concentration can be detected, for example, as described in Example 2, below. Absolute cAMP levels can be detected by obtaining a RET measurement in the assay system and comparing it to a standard curve obtained in vitro.

In some embodiments, steady-state RET measurements are first obtained and then measurements are taken after addition of a test compound to the assay system. Test compounds can be used, for example, to increase cAMP concentration to make it easier to detect cAMP in a particular subcellular compartment or to monitor the effect of the test compound on cAMP concentration (e.g., in drug-screening methods). Test compounds can be pharmacologic agents already known in the art to affect cAMP levels or can be compounds previously unknown to have such an activity. Compounds known to affect cAMP levels include, for example, β-adrenergic receptor agonists (e.g., norepinephrine, epinephrine, isoproterenol, sulfonterol, metaproterenol, SB-251023), β-adrenergic receptor antagonists (e.g., propranolol, butoxamine, practolol, alprenolol, pindolol, nadolol, metaprolol, SR-59230A), direct or indirect activators of adenylate cyclase (e.g., forskolin, prostalglandin $E_1$), cAMP analogs (e.g., 8-(4-chloro-phenylthio)-2'-O-methyl adenosine 3',5'-monophosphate; $N^6$,2'-O-dibutyryl cyclic adenosine 3',5'monophosphate ($Bt_2$cAMP)), and photolytic release agents (e.g., P-(4,5-dimethoxy-2-nitrobenzyl) adenosine 3',5'-monophosphate, and phosphodiesterase inhibitors such as 3-isobutyl-1-methylxanthine).

Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

High Throughput Assays

Because of their expanded dynamic range, cAMP reporters of the invention can be used advantageously in high throughput analysis of potential pharmacological agonists and antagonists. High throughput assays have sufficient signal amplitude (up to a 35% change in the case of stable cell lines) and tight error bars (see FIG. 9) to distinguish readily the effects of a series of drugs and drug-combinations. The high throughput assay format complements single-cell imaging approaches and can be used to investigate the complexity of cAMP signaling. High throughput assays can be used to screen test compounds to determine their effect on cAMP production and degradation. The methods also are useful for defining previously unknown mechanisms for established drugs. New drug candidates that target G protein coupled receptors, G proteins ($G_s$, $G_i$), phosphodiesterases, and adenylyl cyclase can be identified. The methods can also be used diagnostically.

A typical assay employs a 96-well plate format, although other formats can be used (e.g., 192- or 384-well plates). Embodiments of high throughput assays are described in Examples 9 and 12. High throughput assays which use cells expressing a cAMP reporter of the invention are particularly useful. Cellular assays systems negate the need to determine appropriate cofactors for an intended target prior to screening. Cellular assays also ensure that the active compounds already possess adequate solubility, membrane permeability, stability, and the ability to act within the biological complexity of the cell, so that false hits with incompatible properties can be eliminated in the early screening stages.

Fluorescence activated cell sorting (FACS) is well-suited for use with high throughput methods of the invention. For example, emission ratios of cyan-to-yellow for individual cells are detected during the first sorting; not all cells will have the same emission ratio, and a distribution for the whole population will be plotted. The cells can be contacted with a test compound, and emission ratios of individual cells can be detected again during the second sorting. The difference in emission ratios, typically presented as a shift in the distribution, reflects the changes in cAMP concentration.

In some embodiments, steady-state RET measurements are first obtained and then measurements are taken after addition of a test compound to the assay system. Test compounds can be used, for example, to increase cAMP concentrations activity or to monitor the effect of the test compound on cAMP concentrations (e.g., in drug-screening methods). Test compounds can be pharmacologic agents already known in the art to affect cAMP levels or can be compounds previously unknown to have such an activity. Compounds known to affect cAMP levels include, for example, β-adrenergic receptor agonists (e.g., norepinephrine, epinephrine, isoproterenol, sulfonterol, metaproterenol, SB-251023), β-adrenergic receptor antagonists (e.g., propranolol, butoxamine, practolol, alprenolol, pindolol, nadolol, metoprolol, SR-59230A), direct or indirect activators of adenylate cyclase (e.g., forskolin, prostalglandin $E_1$), cAMP analogs (e.g., 8-(4-chloro-phenylthio)-2'-O-methyl adenosine 3',5'-monophosphate; $N^6$,2'-O-dibutyryl cyclic adenosine 3',5'monophosphate ($Bt_2$cAMP)), and photolytic release agents (e.g., P-(4,5-dimethoxy-2-nitrobenzyl) adenosine 3',5'-monophosphate, and phosphodiesterase inhibitors such as 3-isobutyl-1-methylxanthine).

Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

Kits

The invention provides kits comprising one or more cAMP reporters of the invention.

The kits also may provide all or a subset of the reagents that are required for practicing the invention. The kits may comprise written instructions, in paper or electronic form, or a reference to an on-line set of instructions. The instructions may contain data against which the results determined using the kit can be compared. Containers which hold the components of any given kit can vary. The kits may be divided into compartments or contain separate vessels for each component. The components may be mixed together or may be separated. Optional components of the kit include means for collecting, processing, and/or storing test samples.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Preparation and Function of cAMP Reporters

We generated a number of proteins by fusing the amino terminus of various Epac truncations to ECFP and the carboxyl terminus to citrine, an improved version of YFP (FIG. 1). Full length Epac1 (1-881, SEQ ID NO:1) and truncated forms of Epac2, T316-A501 (amino acids 316-501 of SEQ ID NO:20) and P350-A501 (amino acids 350-501 of SEQ ID NO:20), were created by PCR using Epac1 (de Rooij et al., *Nature* 396, 474-77, 1998.) or Epac2 (SEQ ID NO:20; Ozaki et al., *Nature Cell Biology* 2, 805-11, 2000) as the templates. In one construct, ECFP and citrine were fused together with a domain (amino acids P350-A501 of SEQ ID NO:20) containing the second cyclic nucleotide monophosphate-binding domain from Epac2 and a C-terminal lid (the α-helix that stabilizes the cAMP-binding site) (FIG. 1). Mutation R522E was incorporated by the QUICKCHANGE® method (Stratagene). Enhanced cyan fluorescent protein (ECFP) and citrine were fused to the N and C terminal ends of the individual gene constructs (FIG. 1). The constructs were first generated in pRSET B (Invitrogen) and subcloned into pcDNA3 (Invitrogen) behind a Kozak sequence for mammalian expression.

For nuclear targeting, the nuclear localization signal PKKKRKVEDA (SEQ ID NO:5) was added to the C terminus. Localization to the mitochondrial matrix was achieved by fusing the first 12 amino acids of subunit IV of human cytochrome oxidase c and a four-residue linker (SEQ ID NO:8) to the N terminal of the construct. For plasma membrane targeting of ICUE1, the sequence KKKKKSKT-KCVIM (SEQ ID NO:6) was inserted at the. C terminus. The signal sequence MAIQLRSLFPLALPGMLALLGWWW- FFSRKK (SEQ ID NO:7) was inserted at the N terminus for targeting ICUE to mitochondria.

EXAMPLE 2

Cell Culture and Imaging

Cell Culture. HEK-293, HeLa and PC12 cells were plated onto sterilized glass coverslips in 35 mm dishes and grown to 50-90% confluency in DMEM (10% FBS at 37° C., 5% $CO_2$). Cells were then transfected with FuGENE-6 transfection reagent (Roche) or calcium phosphate and allowed to grow for 12-24 hours before imaging. Colocalization studies were performed by incubating transfected HEK-293 cells with MitoTracker Red 580 or Hoechst 33342 cell-permeable dyes (Molecular Probe) for staining mitochondria or nucleic acids, respectively.

Imaging. Cells were washed twice with Hanks' balanced salt solution buffer after 12- to 24-h incubation at 37° C. culture medium. Cells were maintained in buffer in the dark at room temperature with addition of isoproterenol (Aldrich), forskolin (Calbiochem), Prostaglandin $E_1$ ($PGE_1$) (Sigma), and 8-(4-chloro-phenylthio)-2'-O-methyl adenosine 3',5'-monophosphate (8-pCPT-2'-O-Me-cAMP) (Axxora Biolog) as indicated. Cells were also treated with P-(4,5-dimethoxy-2-nitrobenzyl) adenosine 3',5'-monophosphate (DMNB-cAMP) (Molecular Probe). Uncaging of cAMP was performed as previously described (Zhang et al., *Proc. Natl. Acad. Sci. USA* 98, 14997-15002, 2001.).

Cells were imaged on a Zeiss Axiovert 200M microscope with a cooled charge-coupled device camera MicroMAX BFT512 (Roper Scientific) controlled by METAFLUOR 6.2 software (Universal Imaging). Dual-emission ratio imaging used a 420DF20 excitation filter, a 450DRLP dichroic mirror and two emission filters (475DF40 for ECFP, 535DF25 for citrine) alternated by a filter changer Lambda 10-2 (Sutter Instruments). Exposure time was 100-500 ms and images were taken every 8-30 s. Fluorescent images were background-corrected by subtracting autofluorescence intensities of untransfected cells (or background with no cells) from the emission intensities of fluorescent cells expressing reporters. The ratios of cyan to yellow emissions were then calculated at different time points and normalized by dividing all ratios by the emission ratio just prior to stimulation therefore setting the basal emission ratio to 1.

FRET efficiency was determined by acceptor photobleaching as reported (Miyawaki & Tsien, *Methods Enzymol.* 327, 472-500, 2000). Briefly, citrine was photobleached at the end of the experiment by intense illumination with a 525DF40 filter. ECFP fluorescence intensities before ($F_d$) and after citrine photobleaching ($F_d$) and the equation $E=1-(F_{da}/F_d)$ were then used to calculate the FRET efficiency.

EXAMPLE 3

Function of cAMP Reporters

A cAMP reporter in which ECFP and citrine were fused together with a domain (P350-A501; amino acids 350-501 of SEQ ID NO:20) containing the second cyclic nucleotide monophosphate-binding domain from Epac2 and a C-terminal lid was expressed in HEK-293 cells. This reporter showed variable ratios of cyan to yellow emissions which are inversely correlated with expression level of the protein. This concentration dependence indicates intermolecular FRET between different reporter molecules that may occur due to oligomerization or aggregation (Zacharias et al., *Science* 296, 913-16, 2002). Upon cAMP elevations, this protein did not show a cAMP-dependent FRET change. We incorporated a larger portion of Epac2 sequence N-terminal to the binding domain (T316-A501; amino acids 316-501 of SEQ ID NO:20) (FIG. 1) and obtained a construct that showed more homogeneous emission ratios and a 5% increase in emission ratio of cyan to yellow upon cAMP elevations.

Figure 2:
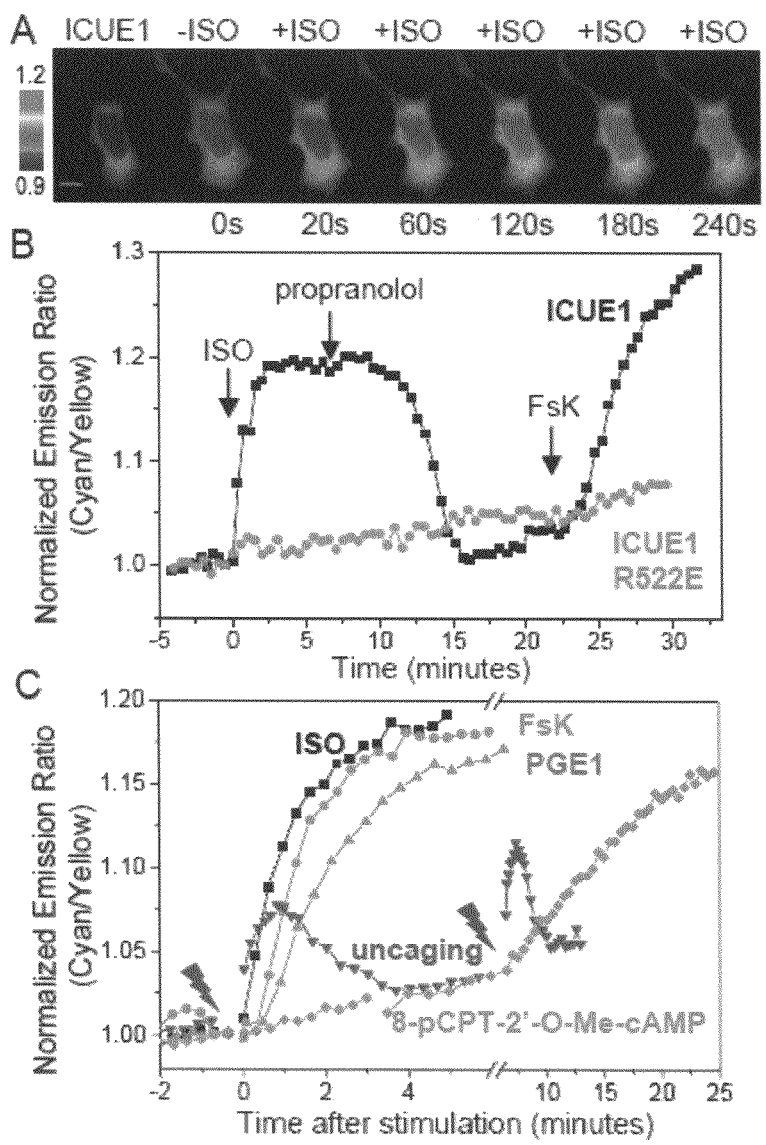
FIGS. 2A-C. Responses of ICUE1 to changes in cellular cAMP levels.

To improve the dynamic range of the response and to develop a reporter for Epac activation, we sandwiched the full-length Epac1 between ECFP and citrine (FIG. 1). When this reporter (designated as ICUE1) was transfected in HEK-293 cells, the fluorescence was uniformly distributed in the cytosolic compartment in 60% of the cells (FIG. 2A, leftmost image). In the remaining 40% of the cells, the protein was localized to perinuclear region or mitochondria, consistent with our previous observation using full-length Epac1 fused to YFP (Qiao et al., *J. Biol. Chem.* 277, 26581-86, 2002). A similar expression pattern was also observed in HeLa and PC12 cells.

Stimulation of endogenous β-adrenergic receptor (β-AR) with isoproterenol generated a FRET decrease in HEK293 cells expressing ICUE1, resulting in an increase in the ratio of cyan to yellow emissions (FIGS. 2A and 2B). The change in emission ratios was detectable within several seconds and reached a plateau of 16.8%±1.0 (average value±S.E.M, n=8) signal increase within 1.5-3 min. This FRET change consisted of reciprocal decreases in yellow and increases in cyan emission and the FRET efficiencies were measured by acceptor photobleaching to be 29%±3 and 21%±1 (n=3), respectively, before and after isoproterenol stimulation. The presence of propranolol, a β-adrenergic-receptor antagonist, prevented the isoproterenol-stimulated response.

We next tested if the FRET response was reversible. Addition of 10 μM propranolol after the isoproterenol-stimulated response reached the plateau resulted in an initial decrease in emission ratio of cyan to yellow in 2-3 minutes, and a full recovery over 6-8 minutes. Removal of isoproterenol had the same effect. Finally, a second rise in emission ratio was induced by addition of forskolin to activate adenylate cyclase (AC) and elevate cAMP. The change in emission ratio reached a plateau in 3-5 minutes (FIG. 2B).

To verify the FRET response is due to cAMP binding, we generated a variant of the reporter that carries a point mutation in the cAMP binding domain. Arginine 279 in Epac1 is a conserved residue that contributes to cAMP binding (Rehmann et al., *Nat. Struc. Biol.* 10, 26-32, 2003). EpacR279E is defective in cAMP binding (de Rooij et al., *Nature* 396, 474-77, 1998; Mei et al., *J. Biol. Chem.* 277, 11497-504, 2002), and mutation of the same Arginine to Glutamate (R522E) in the reporter completely abolished the FRET change induced by isoproterenol and forskolin (FIG. 2B, n=7).

Figure 12:
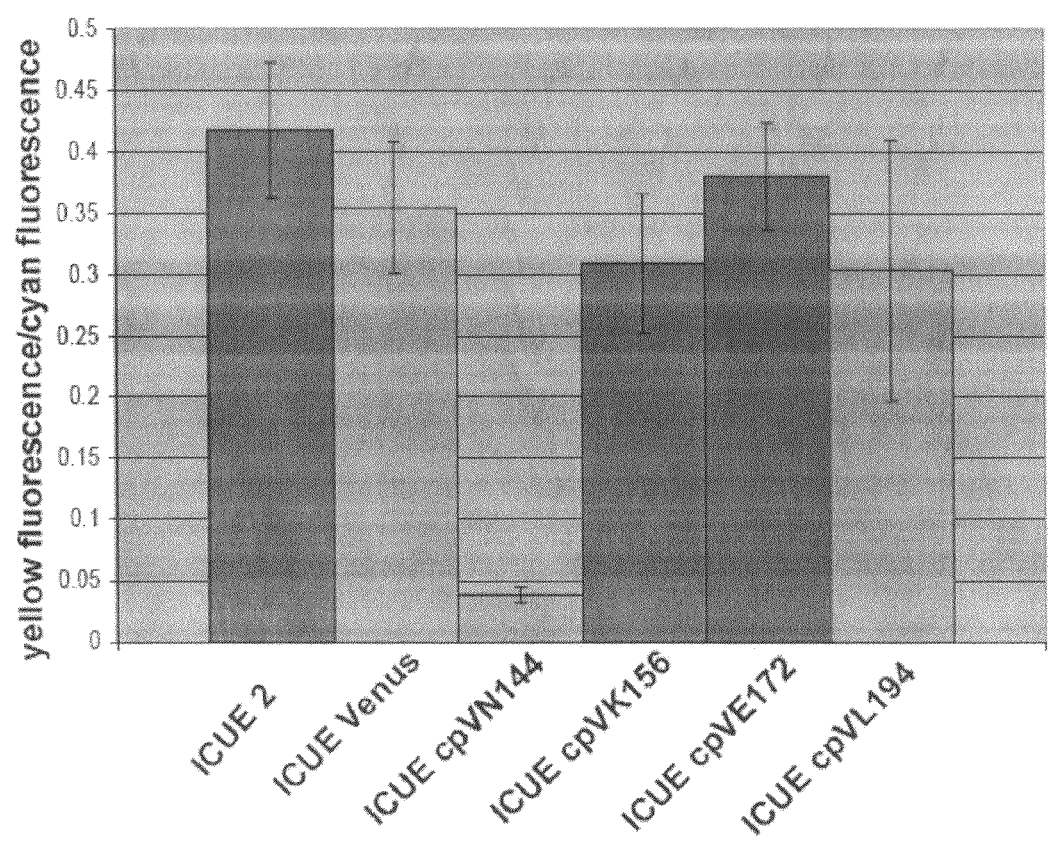
FIG. 12. Ratios of YFP fluorescence intensities to CFP fluorescence intensities for ICUE constructs. Average values of YFP intensities were divided by the average intensities of CFP after YFP photobleaching. YFP photobleaching was achieved by irradiating without neutral density filters through a 525DF40 filter (Chroma Technologies).
Figure 13:
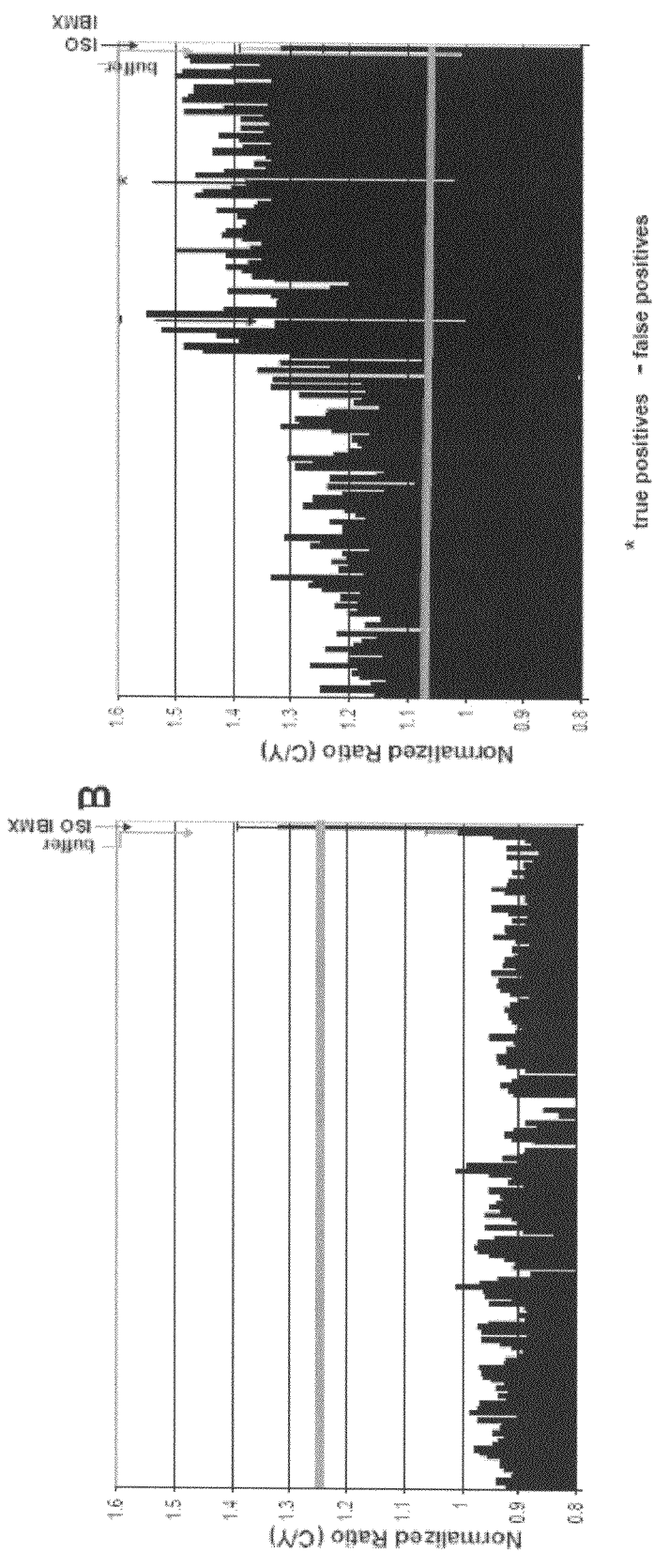
FIG. 13. High-throughput screening with ICUE3.

Different means of elevating intracellular cAMP revealed different kinetics for the FRET response (FIG. 2C). As shown in FIGS. 2B and 2C, activation of β-AR with a selective agonist such as isoproterenol (10 μM) induced decreases in FRET in 1.5-3 minutes, while stimulation of adenylate cyclase required slightly longer treatment with forskolin (3-5 minutes) to produce a maximal increase in emission ratios (19.6%±1.0 response, n=8) (FIG. 2C). Addition of 10 μM prostaglandin E1 ($PGE_1$) to increase cAMP levels (Rich et al., *Proc. Natl. Acad. Sci. USA* 98, 10349-54, 2001) induced a FRET response (13.3%±0.9, n=7) within 3-5 minutes, noticeably delayed compared to the response induced by isoproterenol (FIG. 2C). A newly characterized analogue of cAMP, 8-pCPT-2'-O-Me-cAMP, specifically activates Epac but not PKA (Enserink et al., *Nat. Cell Biol.* 4, 901-06, 2002). This cAMP analog, when administrated at 300 μM, required 10-15 minutes to produce a half-maximal increase in emission ratios ($t_{1/2}$) (FIG. 2C, 12.8%±0.9, n=6).

The fastest intracellular responses were generated by photolytic release ("uncaging") of cAMP from a membrane-permeant ester, DMNB-cAMP (Nerbonne et al., Nature 310, 74-76, 1984). Cells expressing ICUE1 were first incubated with 100 μM DMNB-cAMP for 3 minutes and were exposed to UV to uncage the cAMP intracellularly. Flash of 5 seconds acutely increased the emission ratio by 4.7%±0.7 (n=8) in just 15-30 seconds (FIG. 2C). The response was then quickly reversed due to the degradation of uncaged cAMP by phosphodiesterase (PDE). The slower time courses of the other responses are presumably due to rate-limiting steps in activating adenylate cyclase and accumulating sufficient cAMP, rather than the kinetics of cAMP binding to Epac1, or the FRET response of the reporter.

EXAMPLE 4 cAMP Dynamics within Subcellular Compartments

Figure 3:
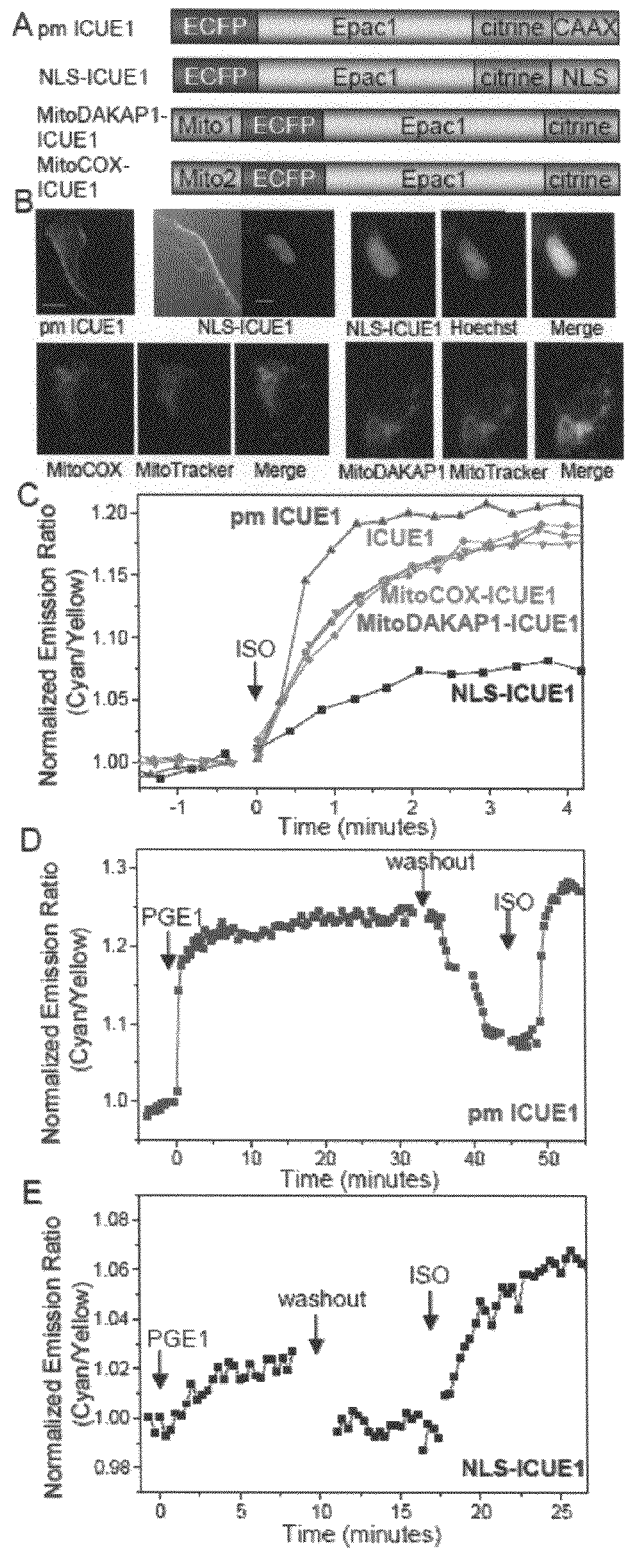
FIGS. 3A-E. Fusions of ICUE1 targeted to various subcellular locations.

To directly monitor cAMP dynamics at different subcellular locations inside cells, we prepared several fusions of ICUE1 to various specific targeting motifs (FIG. 3A). To localize the reporter to the plasma membrane, we fused the plasma membrane-targeting signal of small guanosine triphosphatase K-ras4B (Roy et al., Biochem. 39, 8298-307, 2000) to the C terminus of ICUE 1. This targeting motif combined a farnesylated cysteine residue with a strongly polybasic sequence and effectively targeted the reporter to the plasma membrane (FIG. 3B).

As shown in FIG. 3C, plasma membrane targeted ICUE1 generated a FRET response of 18.3%±1.2 (n=8) upon stimulation with isoproterenol. The response time ($t_{1/2}$=24.9 s±2.8, n=8) was shortened by 40% compared to the time course for the cytoplasmically-distributed ICUE1 ($t_{1/2}$=40.5 s±3.3, n=8), while both plasma membrane-targeted and cytoplasmically-distributed ICUE1 generated rapid responses upon whole-cell cAMP uncaging. These results indicate that this delay in response of untargeted ICUE1 is not due to the intrinsic kinetic properties of the localized reporters, but most likely due to restricted release of cAMP from the plasma membrane to cytosol (Rich et al., J. Gen. Physiol. 116, 147-61, 2000).

EXAMPLE 5 cAMP Dynamics and Epac Activation in Mitochondria

Epac localizes to mitochondria in a subpopulation of cells, but monitoring of cAMP accumulation at mitochondria has not been possible with previous methods. To examine the cAMP dynamics and Epac activation at this subcellular location, we fused two different mitochondria targeting motifs to ICUE1 (FIG. 3A). The first MitoCOX-ICUE1 was generated by fusing the targeting sequence of subunit IV of cytochrome c oxidase (COX) to the N-terminus of ICUE1. This COX sequence delivers fused proteins to the mitochondrial matrix (Hurt et al., EMBO J. 4, 2061-68). As shown in FIG. 3B, MitoCOX-ICUE1 was partially targeted to mitochondria (Filippin et al., J. Biol. Chem. 278, 39224-34, 2003), showing partial colocalization with a cell permeable mitochondrial dye, MitoTracker.

Activation of β-AR by isoproterenol generated a FRET response (19.0%±1.6, n=5) in the punctate mitochondria structure within 2-3 minutes ($t_{1/2}$=40.4 s±7.3, n=5), indicating that cAMP can enter mitochondria and accumulate in the matrix. In a second mitochondria-targeted ICUE1 (MitoDAKAP1-ICUE1), a mitochondria targeting motif taken from the N-terminal sequence of DAKAP1a (Ma & Taylor, J. Biol. Chem. 277, 27328-36, 2002) effectively targeted ICUE1 to mitochondria (FIG. 3B), where the isoproterenol stimulated FRET response (14.5%±1.5, $t_{1/2}$=42.4 s±2.5, n=6) is similar to the cytosolic response (FIG. 3C).

When fused to a nuclear localization signal (NLS), ICUE1 was appropriately targeted to the nucleus (FIG. 3B), where its response to isoproterenol stimulation was smaller (5.6%±0.5, n=12) than the 16.8%±1.0 FRET change for cytoplasmically-distributed ICUE1 (FIG. 3C). Stimulation with bicarbonate to activate endogenous soluble adenylate cyclase in HEK-293 cells did not generate a cAMP-dependent response in the nucleus, possibly due to limited copy numbers of soluble AC in this cell type or the sensitivity of the detection. Interestingly, the isoproterenol-stimulated response in the nucleus is not delayed ($t_{1/2}$=38.5 s±3.5, n=12) compared to that from untargeted ICUE1. This indicates that the available pool of cAMP in the nucleus, while possibly smaller, is not kinetically crippled due to the fast diffusion of cAMP from cytosol to nucleus.

To test if activation of different receptors leads to production of different pools of cAMP, we compared the cAMP responses induced by $PGE_1$ and isoproterenol at different subcellular sites. At the plasma membrane, addition of $PGE_1$ generated a 12.6%±0.9 (n=8) emission ratio increase within 2-3 minutes. Surprisingly, sustained stimulation with 10 μM $PGE_1$ did not produce a transient response as observed previously using cyclic nucleotide-gated ion channels (Rich et al., Proc. Natl. Acad. Sci. USA 98, 13049-54, 2001). In contrast, the response at the plasma membrane is sustained until removal of $PGE_1$ (FIG. 3D). Variable cellular PDE activities may be responsible for this discrepancy.

After removal of $PGE_1$, a second response of similar amplitude was induced by stimulation with isoproterenol. Both untargeted and mitochondria targeted ICUE1 showed similar responses to $PGE_1$ and isoproterenol. In the nucleus, $PGE_1$ also stimulated a small response (3.4%±0.4, n=13), noticeably a few percentages smaller than that induced by isoproterenol in the same cell (FIG. 3E).

EXAMPLE 6

Simultaneous Imaging of cAMP Dynamics and PKA Phosphorylation

Soluble AC and regulatory and catalytic subunits of protein kinase A (PKA) coexist in the nucleus of mammalian cells (Zippin et al., J. Cell Biol. 164, 527-34, 2004). The activation of bicarbonate-responsive soluble AC in the nucleus led to a rapid increase in PKA-dependent phosphorylation, which was detectable within two minutes. The immediate presence of a nuclear pool of cAMP following β-AR activation raised the question whether this pool of cAMP could produce functional PKA responses in the nucleus. Here, we took advantage of the targeted cAMP indicators and a PKA activity reporter, AKAR (Zhang et al., Proc. Natl. Acad. Sci. USA 98, 14997-5002, 2001), to examine the temporal correlation of cAMP dynamics and PKA activation within single living cells.

Figure 4:
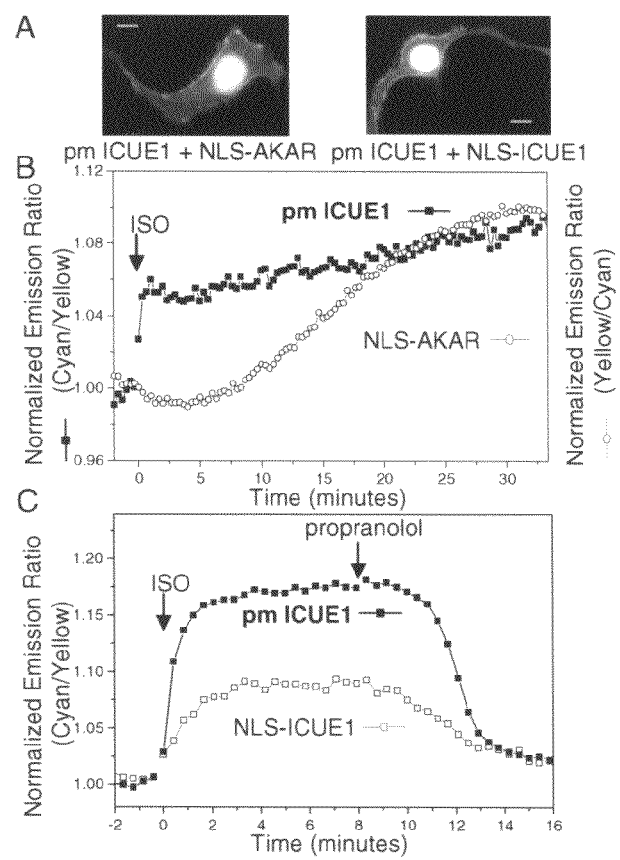
FIGS. 4A-C. Simultaneous imaging of cAMP reporters targeted to different subcellular locations.
Figure 5:
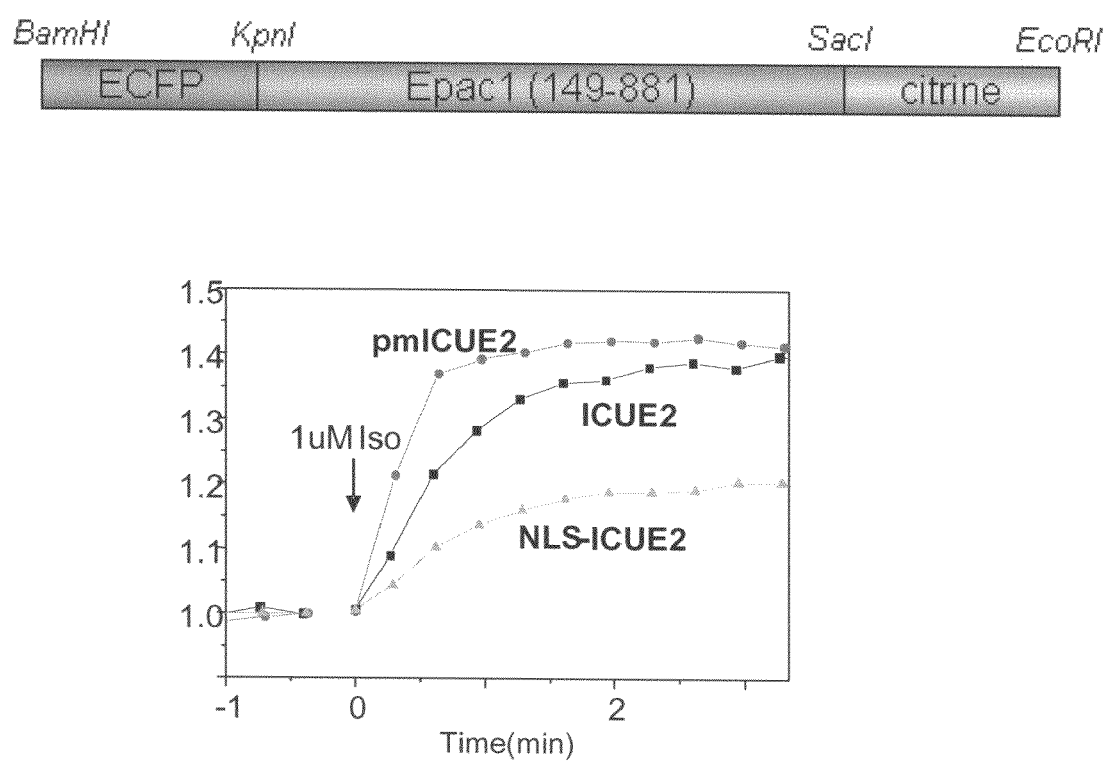
FIG. 5. Graph showing emission ratio time courses for ICUE2 and targeted versions of ICUE2. Y axis, normalized emission ratio (cyan/yellow).
Figure 6:
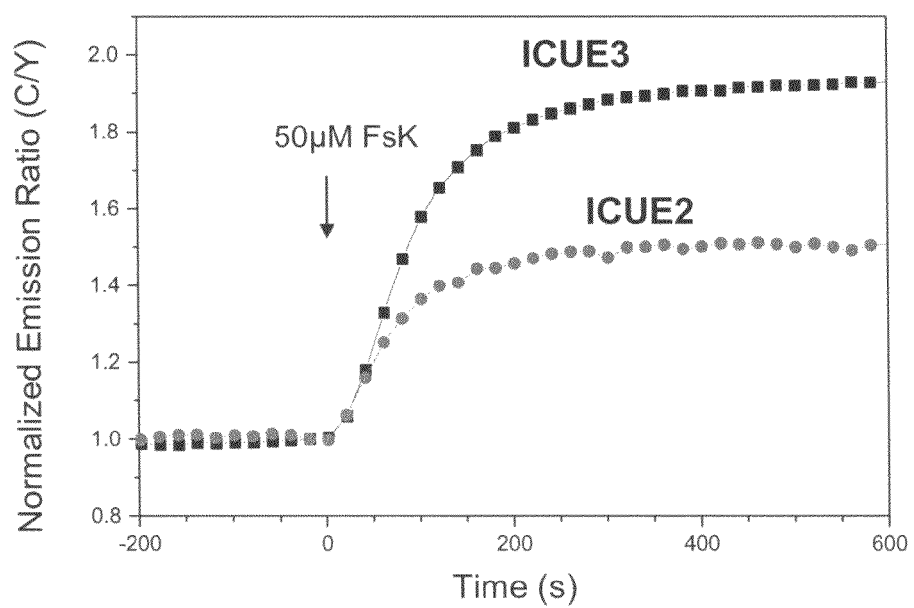
FIG. 6. Graph showing emission ratio time courses for ICUE2 and ICUE3.

We co-expressed the plasma membrane-targeted ICUE1 and nuclear-localized AKAR in HEK-293 cells (FIG. 4A). An immediate increase in emission ratios of cyan to yellow occurred at the plasma membrane upon stimulation with isoproterenol, indicating an acute rise in cAMP. The emission ratio in the nucleus did not increase in the same time frame. After a delay of 5-10 minutes, in the presence of the sustained cAMP response a gradual increase in ratio of yellow to cyan emissions occurred and reached a plateau in 20-30 minutes. Untargeted AKAR generated acute responses in 2-3 minutes in the cytosol of HEK-293 cells upon stimulation with isoproterenol. This is consistent with acute cytosolic AKAR responses upon cAMP elevations we previously reported (Zhang et al., 2001). Therefore, the delay in response indicates that PKA phosphorylation in the nucleus does not occur immediately following cAMP production (FIG. 4B). This delayed nuclear response of PKA phosphorylation is consistent with a slow diffusional translocation of the catalytic (C) subunit of PKA into the nucleus following the dissociation of catalytic and regulatory subunits in the cytoplasm upon cAMP elevation (Harootunian et al., *Mol. Cell Biol.* 4, 993-1002, 1993; Meinkoth et al., *Proc. Natl. Acad. Sci. USA* 87, 9595-99, 1990).

As a control experiment, we also recorded cAMP responses from single cells co-expressing both plasma membrane-targeted and nuclear-localized ICUE1 for direct comparison of the cAMP dynamics at the plasma membrane and in the nucleus. As shown in FIG. 4C, isoproterenol stimulated an acute cAMP response at the plasma membrane followed by a response in the nucleus, which reached the plateau in 2-3 minutes. This is consistent with data obtained from separate cells expressing either targeted reporter indicating that ICUE reporter molecules do not notably perturb cAMP distribution throughout the cell. This acute nuclear cAMP response is in sharp contrast to the delayed response of PKA phosphorylation in the nucleus, which requires 20-30 minutes to reach the maximum. Thus, the presence of this nuclear pool of cAMP immediately following cAMP production is not sufficient to generate a detectable phosphorylation of AKAR by PKA within the nucleus. This lack of immediate PKA response could be due to either the absence of the PKA holoenzyme in the nucleus or insufficient activation of soluble AC-coupled PKA by this pool of cAMP. In this case, the slow diffusion of the C subunit rather than the fast diffusion of cAMP as the rate-limiting step may provide the temporal control of β-AR-stimulated PKA-dependent phosphorylation in the nucleus.

EXAMPLE 7

Preparation and Function of a cAMP Reporter Comprising a Truncated Epac1 (ICUE2)

In about 40% of transfected cells, untargeted ICUE1 localizes to mitochondria and perinuclear region, which has been documented as the subcellular localization of endogenous Epac1. To create a more uniformly expressed reporter, we deleted the disheveled, Eg1-10, and pleckstrin homology (DEP) domain (amino acids 1-148) which is responsible for this localization. The truncation was generated by PCR amplification of ICUE1 in pRSETB bacterial vector starting from glycine 149 of Epac1 through to the end of citrine using the forward primer shown in SEQ ID NO:15:

5'-CGCGGTACCCCCGTGGGAACTCATGAGATGG-3' and a pRSETB reverse primer. The PCR fragment was then ligated into pcDNA3 mammalian vector containing ECFP. As a result, the truncated reporter, ICUE2, is more diffusible, showing no specific subcellular targeting.

Imaging with ICUE2 in HEK-293 cells revealed a 40-50% increase in cyan/yellow emission ratio upon stimulation of cAMP production with forskolin, compared to a 15-30% response generated by ICUE1. Maximum FRET response was reached in 1.5-3 minutes upon stimulation with isoproterenol, which is on the same time scale as the ICUE1 response. Targeted versions of ICUE2 exhibited the increased dynamic range in cyan/yellow emission ratio as well, therefore improving the signal-to-noise ratio.

ICUE2 also responded to lower concentrations of isoproterenol. We observed FRET responses upon the addition of 0.1 µM, 1 µM, as well as 10 µM isoproterenol, which was the lowest concentration of isoproterenol that generated a FRET response of ICUE 1. The ICUE2 response reverses in an average of 9 minutes once it reaches maximum without addition of β-AR antagonist, propranolol, or washing out of agonist.

EXAMPLE 8

Preparation and Function of a cAMP Reporter Comprising a Circularly Permuted Acceptor Moiety (ICUE3)

The dynamic range of ICUE2 was increased by replacing citrine with a circularly permuted YFP, cpVenus L194 to form a cAMP reporter termed ICUE3. Circular permutation introduces new N and C termini to a protein and can improve the dynamic range of FRET-based reporters by altering the relative orientation of fluorescent proteins (Nagai et al., 2004).

Upon stimulation with the adenylate cyclase activator forskolin, ICUE3 produced a maximum 100% increase in cyan/yellow emissions ratio in HEK-293 cells. Like ICUE2, the ICUE3 response is also reversible when cells are stimulated by the β-adrenergic receptor agonist, isoproterenol.

EXAMPLE 9

High Throughput Assay Using ICUE2

HEK293 cells which stably express ICUE2 ("ICUE2 stable HEK293 cells") were grown to confluency in 10 cm dishes in DMEM, 10% FBS, 1% penicillin/streptomycin, and 250 µg/ml G418. HEK-293 cells were transfected with cDNA encoding ICUE2 using calcium phosphate at 40% confluency and allowed to grow for 40 hours. Cells were removed from the dish using 0.05% trypsin, spun down, and replaced with fresh media. ICUE2 stable HEK293 cells were counted on a hemocytometer using trypan blue stain. One hundred fifty thousand (150,000) cells were plated per well on a 96-well clear bottom assay plate in a total of 0.2 ml of media per plate and allowed to double once. Media was removed, cells were washed with Hanks buffered salt solution (HBSS) and then covered with 0.05 ml of HBSS per well. In a separate sterile plate, appropriate drugs were added to each well containing HBSS for a total volume of 0.05 ml.

Plate reading used a 420DF20 excitation filter and two emission filters (470DF40 for cyan and 535DF25 for yellow). A baseline was established in three cycles, each consisting of a full plate reading of yellow intensity, followed by a reading of cyan intensity. Cells were then treated with isoproterenol (ISO; Aldrich), forskolin (Calbiochem), H89, propranolol, and 3-isobutyl-1-methylxanthine (IBMX) as indicated. Readings were taken in six or twenty additional cycles. Each cycle lasted 60 to 145 sec. Baseline FRET ratios were calculated as the average ratio of yellow/cyan for each well before the addition of drug. FRET change was calculated as the percent increase of FRET ratio over baseline for each well during a given cycle. The FRET changes of all wells having undergone the same drug treatment were then averaged within each cycle, and that cycle was correlated with time.

Figure 7:
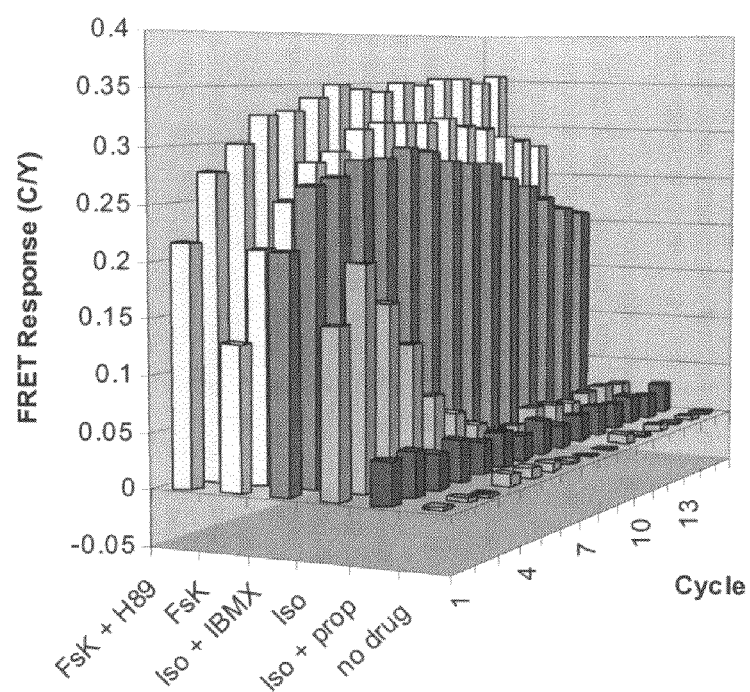
FIG. 7. High throughput analysis of the effect of a combination of various small molecules was performed using stable ICUE2 HEK293 cells in a 96-well plate format. The ratios of cyan emission/yellow emission were calculated before and after drug additions, and the average changes in emission ratios were plotted. Different drugs were used in the following concentrations: 1 µM isoproterenol (Iso), 10 µM H-89, 100 µM IBMX, and 50 µM forskolin (FSK). 1 cycle=90 seconds.
Figure 8:
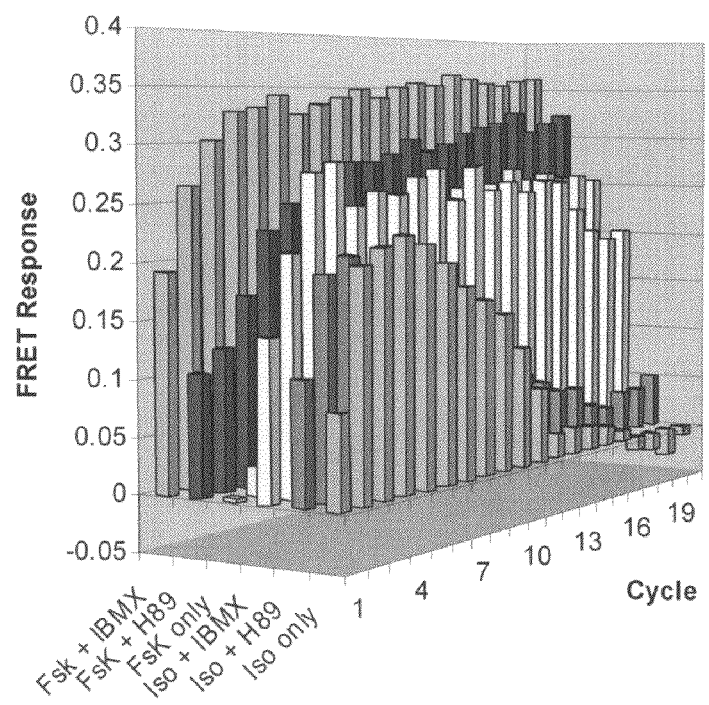
FIG. 8. High throughput analysis of the effect of a combination of various small molecules was performed using stable ICUE2 HEK293 cells in a 96-well plate format. The ratios of cyan emission/yellow emission were calculated before and after drug additions, and the average changes in emission ratios were plotted. Different drugs were used in the following concentrations: 1 µM isoproterenol (Iso), 10 µM H-89, 100 µM IBMX, and 50 µM forskolin (FSK). 1 cycle=60 seconds.

ICUE2 stable HEK293 cells were treated with an array of drugs as shown in FIGS. 7 and 8 (also see Table 1). Addition of 1 µM ISO induced transient responses, consistent with single-cell imaging data. Addition of 100 μM IBMX, an inhibitor of phosphodiesterases (PDEs), increased the amplitude and sustained the responses, indicating that PDEs play an important role in switching off cAMP signaling.

When cells were treated with 50 μM FSK, sustained responses were observed for cAMP accumulation. Treatment of cells with both 50 μM FSK and 10 μM H89 increased the amplitude of ICUE2 signal, giving an emission ratio change of 35%. It was previously shown that protein kinase A (PKA) can activate some PDE isoforms. Further studies can be carried out to elucidate PDE roles in controlling intracellular cAMP levels and PKA activities.

Figure 9:
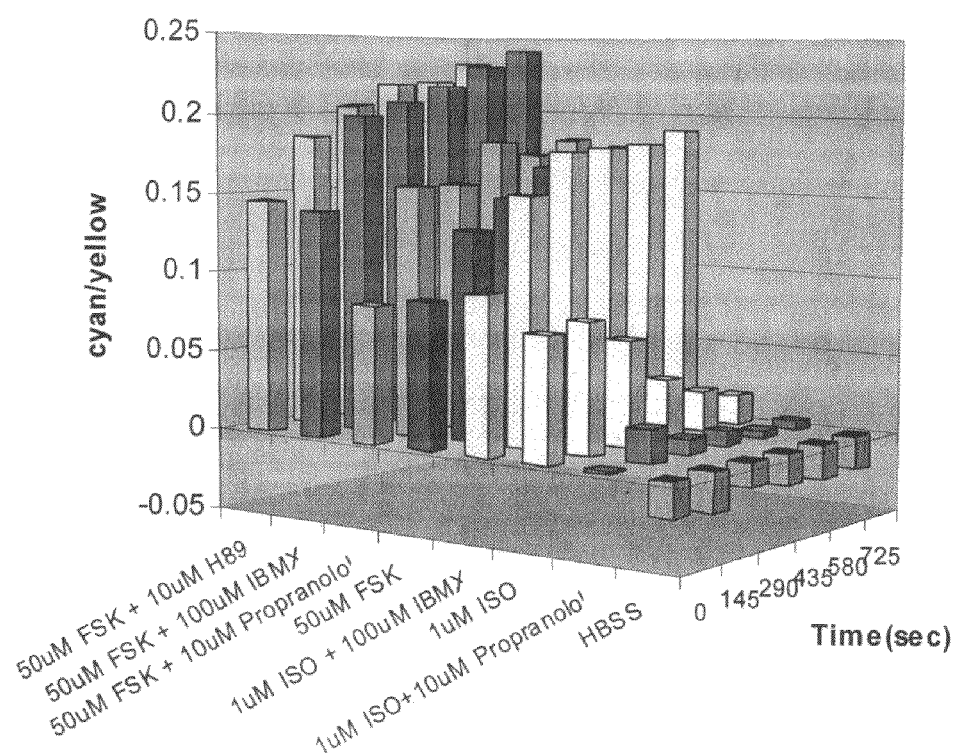
FIG. 9. High throughput analysis of the effect of a combination of various small molecules was performed using HEK293 cells expressing ICUE3 in a 96-well plate format. The ratios of cyan emission/yellow emission were calculated before and after drug additions, and the average changes in emission ratios were plotted. Different drugs were used in the following concentrations: 1 µM isoproterenol (Iso), 10 µM H-89, 100 µM IBMX, 50 µM forskolin (FSK), and 100 µM propranolol (PRO).

HEK293 cells transiently transfected with ICUE3 showed similar results, although with slightly smaller responses of up to 25% change in emission ratio (FIG. 9 and Table 2). The ISO-stimulated responses were inhibited by the presence of 10 mM propranolol (PRO), a general β-adrenergic receptor antagonist. As a negative control, 10 μM PRO had no effect on the FSK response of ICUE3. As another negative control, addition of the buffer with no drugs generated minimal changes in emission ratios.

This example demonstrates that the cAMP reporter ICUE2 and ICUE3 can be used in high throughput analysis of pharmacological agonists and antagonists. An assay using a 96-well format has sufficient signal amplitude (up to 35% change in the case of stable cell lines) and tight error bars (FIG. 9) to distinguish the effects of a series of drugs and drug combinations. Thanks to the reversibility of the reporters, transient responses can be distinguished from sustained responses.

EXAMPLE 10

Cell Culture and Imaging of cAMP Reporter-Expressing Cells

Figure 10:
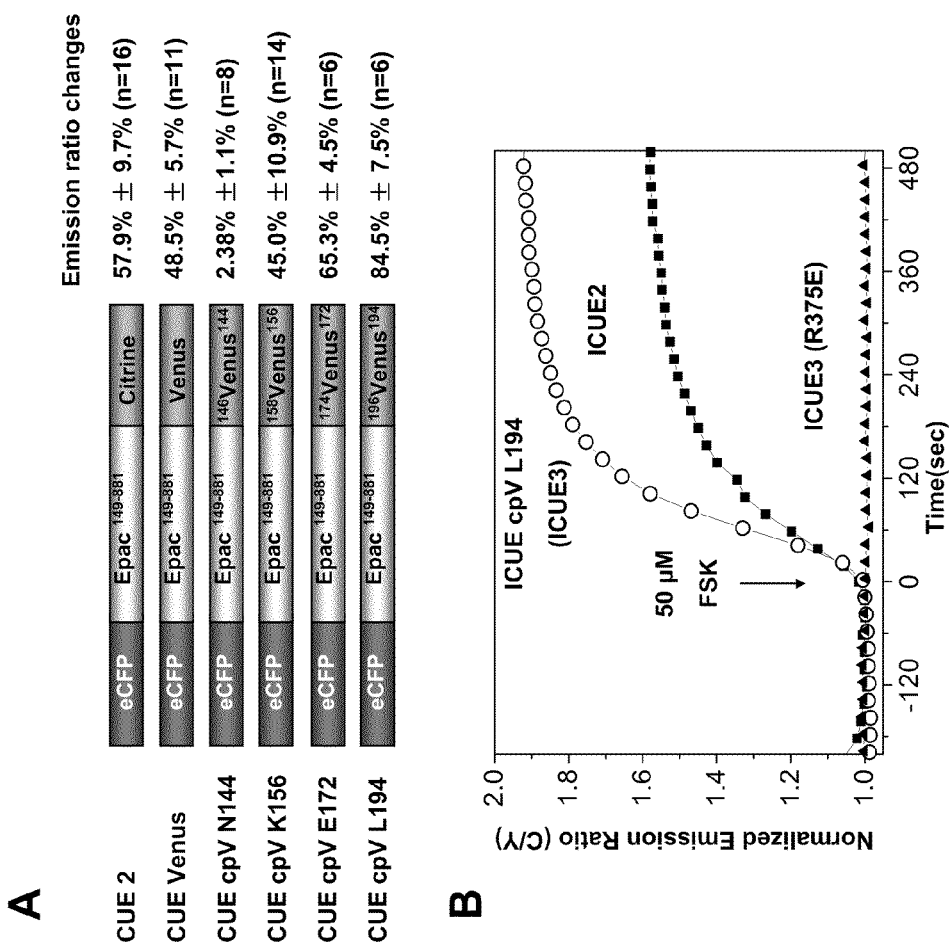
FIG. 10. Development of improved ICUE.

We incorporated cpV N144, cpV E172, cpV K156, and cpV L194 (ICUE3) into ICUE2 using PCR amplification (FIG. 10). Within the cpVenus (cpV) gene, the first residue is a methionine followed by residue P196 in the case of cpV L194, which is named by the residue at the new C-terminus. ICUE3 R373E was generated by the QUICKCHANGE® method (Stratagene). All constructs were initially generated in pRSET B (Invitrogen) then subcloned to pcDNA3 (Invitrogen) behind a Kozak sequence for mammalian expression.

Cell culture and imaging. HEK293 cells were plated onto sterilized glass coverslips in 35 mm dishes and grown to ~50% confluency in DMEM containing 10% FBS at 37° C. with 5% $CO_2$. Cells were transfected with calcium phosphate and allowed to grow for 12-24 hours before imaging. After washing once with HBSS, cells were maintained in buffer in the dark at 20-25° C. ISO, FSK, H89, Thapsigargin (Sigma), and phorbol dibutyrate (PDBu, Sigma) were added as indicated. Cells were imaged with a Zeiss Axiovert 200M microscope with a 40×/1.3NA oil-immersion objective lens and cooled CCD camera as described in Ananthanarayanan et al., *Proc. Natl. Acad. Sci. USA* 102, 15081-86, 2005. Briefly, dual emission ratio imaging used a 420DF20 excitation filter, a 450DRLP dichroic mirror, and two emission filters (475DF40 for cyan and 535DF25 for yellow). The ratio of cyan-to-yellow emissions were then calculated at different time points and normalized by dividing all ratios by the emission ratio before stimulation, setting basal emission ratio as 1. FRET efficiency was determined by acceptor photobleaching as reported in Miyawaki & Tsien, *Methods Enzymol* 327, 472-500, 2000.

Live cell plate reading. HEK293 cells were transfected with cDNA encoding ICUE reporters using calcium phosphate at 40% confluency and allowed to grow for 40 hours. Cells were then trypsinized and plated in a Costar 3603 96-well assay plate (Corning) at a density of 150,000 cells per well. After incubation for another 24 hours, cells were washed once with HBSS and left in 150 μl HBSS at 20-25° C. Fluorescence reading was taken on a FLUOstar OPTIMA fluorescence microplate reader (BMG Labtechnologies Inc.) using a 420DF20 excitation filter and two emission filters (470DF40 for cyan and 525DF25 for yellow). A baseline was established in three cycles, each consisting of a full plate reading of yellow intensity, followed by a reading of cyan intensity. Each cycle lasted between 64 and 145 seconds. Cells were then treated with ISO, FSK, H89, PRO, or IBMX as indicated in FIG. 10. Readings were taken in additional cycles. FRET change was calculated as the percent increase of emission ratios (cyan-to-yellow) over baseline for each well during a given cycle. To assess the efficacy of the assay, several statistical parameters were calculated, including Z factor, coefficient of variation, and signal-to-noise ratio (Zhang et al., *J. Biomol. Screen.* 4, 67-73, 1999).

HEK293 cells expressing the four constructs individually (cpV N144, cpV E172, cpV K156, and cpV L194) were stimulated with FSK, and average emission ratio changes were calculated. In the case of cpV N144, low yellow fluorescence intensity was observed, yielding a reporter with a reduced dynamic range (FIG. 10A). The cpV E172 and cpV K156 did not significantly change the dynamic range, showing an average response of 65.3%±4.50% (n=6) and 45.0%±10.9% (n=14), respectively. On the other hand, incorporation of cpV L194 showed a more dramatic effect. Upon stimulation with FSK, HEK293 cells expressing ICUE cpV L194 generated an emission ratio change of 76-93% with an average of 84.5%±7.50% (n=6) (FIG. 10B). Thus, this approach of using cpV variants to create variations in the relative spatial orientation of YFP with respect to CFP proved effective for multiple FRET reporters. This improved indicator of cAMP, named ICUE3, maintained the specificity for cAMP, as a loss-of-function mutation in the cAMP binding site (de Rooij et al., *Nature* 396, 474-77, 1998) abolished the FRET response of ICUE3 (FIG. 10B). When Cypet and Ypt were used as the FRET pair, the resulting ICUE construct generated emission ratio changes of up to 110%; experimental variations and reduced fluorescence intensities in HEK-293 cells suggested that additional optimization can be carried out.

EXAMPLE 11

Cell-Based Assay Using ICUE3

Figure 11:
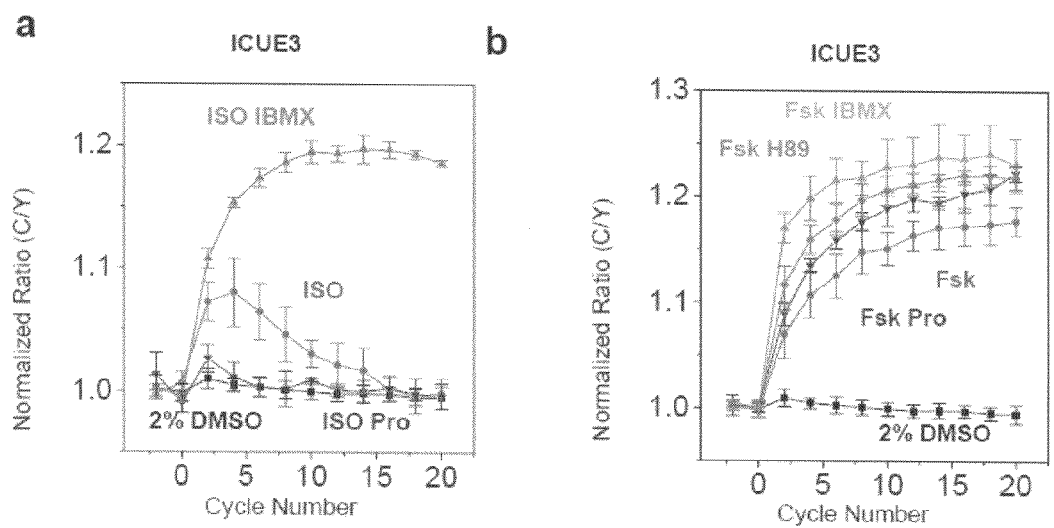
FIG. 11. High throughput cellular assays based on ICUE3. Summary of ICUE3 responses in HEK-293 cells treated with indicated drugs. Ratios of cyan/yellow emission were calculated and plotted versus cycle numbers. Each cycle lasted 145 seconds. Error bars represent standard deviation (n=7). Different drugs were used in the following concentrations: ISO, 1 µM; H-89, 10 µM; 3-isobutyl-1-methylxanthine (IBMX), 100 µM; FSK, 50 µM; and propranolol (Pro), 10 µM.

HEK293 cells expressing ICUE3 were treated with an array of drugs as shown in FIG. 11. Addition of 1 μM ISO induced transient responses, consistent with single cell imaging data, with a maximal response of 8.10%±1.4% (n=7). Such responses can be inhibited by the presence of 10 μM PRO. Addition of 100 μM IBMX sustained the response and increased its amplitude.

When cells were treated with 50 μM FSK, a sustained response was observed for cAMP accumulation (emission ratio change of 17.9%±3.6%; n=7) The presence of 10 μM H89 did not diminish the response of ICUE3. Stimulation by FSK in the presence of H89 appeared to increase the response amplitude of ICUE3, similar to the effect caused by the combination of 50 μM FSK and 100 μM IBMX. As a negative control, 10 μM PRO had no effect on the FSK-stimulated response of ICUE3. Addition of buffer without drugs generated minimal changes in emission ratios.

EXAMPLE 12

High Throughput Cell-Based Assay Using ICUE3

Live cell clinical compound screen. HEK-293 cells expressing ICUE3 were trypsinized and plated in a Costar 3603 96-well plate (Corning) at a density of 150,000 cells per well. After incubation for 24 hours, cells were washed once with HBSS and left in 190 μL of HBSS at 20-25° C. Fluorescence readings were taken as described above with each cycle lasting 90 sec. Following baseline acquisition, cells in each experimental well were treated with a compound from the Johns Hopkins Clinical Compound Library to a final concentration of 10 μM. Control cells were treated with 10 μL of 10% fetal bovine serum (FBS) in a solution of phosphate buffered saline (PBS) at pH 7.4, the solution used to dissolve library compounds. Readings were taken for 10 cycles spanning a time of approximately 15 minutes, after which cells in experimental wells and positive controls were treated with 0.25 μM ISO plus 100 μM IBMX, while negative control cells received 0.5% (v/v) DMSO in HBSS. Ten final cycles were then performed. FRET responses were calculated as described above. Negative control (10% FBS, 0.5% DMSO) and positive control (10% FBS, 0.25 μM ISO) curves were generated. Agonist hits were defined as compounds eliciting responses that are larger than six times of standard deviation above the baseline or 50% of the positive control. Antagonist hits were defined as compounds that decreased the ISO stimulated response by 50% or by six times of the standard deviation. Hits identified based on only one extreme outlier data point in the entire time course were considered false positives. From the plate-reading data, individual channels (yellow and cyan) of all hits were also examined for abnormal changes upon addition of library compounds. An example of detection of a compound with inherent yellow fluorescence is an increase in yellow emission upon excitation with little or no change in cyan emission. Fluorescence or colorimetric properties of compounds were further verified by comparing to literature data or through direct fluorescence measurement. Such hits were labeled as false positives.

Fluorescence microscopy-based secondary screen. A fluorescence microscopy-based secondary screen was used to examine the remaining hits. HEK-293 cells expressing ICUE were followed via fluorescence microscopy before and after treatment with these compounds at a final concentration of 10 μM. Compounds that caused cell rounding, blebbing, lift-up, or severe shrinkage were considered cytotoxic and labeled as false positives. Compounds that did not affect emission ratio dynamics either before or after treatment with isoproterenol (agonist and antagonist secondary screen respectively) were also labeled as false positives. Those that did antagonize or agonize in both primary and secondary screens were labeled as true positives.

TABLE 1

Average percent FRET response ± standard deviation for all cycles (cycle 1-20) for the high throughput analysis shown in FIG. 8. 1 cycle = 60 seconds.

|  | 1 | 2 | 3 | 4 | 5 |
|---|---|---|---|---|---|
| 1 μM Iso | 8.22% ± 5.97% | 20.2% ± 1.69% | 21.59% ± 2.65% | 22.44% ± 2.42% | 21.47% ± 2.92% |
| 1 μM Iso + 10 μM H89 | 10.79% ± 5.97% | 19.28%% ± 5.88% | 20.72% ± 4.61% | 19.28% ± 5.06% | 18.65% ± 5.26% |
| 1 μM Iso + 100 μM IBMX | 14.13% ± 6.98% | 20.97% ± 7.35% | 27.76% ± 4.41% | 28.57% ± 3.83% | 24.63% ± 9.07% |
| 50 μM FsK | 0.36% ± 7.51% | 2.67% ± 4.53% | 8.71% ± 6.66% | 15.29% ± 3.37% | 15.23% ± 6.55% |
| 50 μM Fsk + 10 μM H89 | 10.65% ± 17.5% | 12.54% ± 15.11% | 16.85% ± 9.42% | 22.38% ± 8.4% | 24.66% ± 7.81% |
| 50 μM Fsk + 100 μM IBMX | 19.13% ± 2.68% | 26.42% ± 4.29% | 30.35% ± 6.55% | 32.77% ± 10.52% | 33.24% ± 10.84% |

|  | 6 | 7 | 8 | 9 | 10 |
|---|---|---|---|---|---|
| 1 μM Iso | 19.64% ± 1.73 | 17.36% ± 1.28% | 15.93% ± 2.0% | 14.45% ± 3.55% | 11.07% ± 2.19% |
| 1 μM Iso + 10 μM H89 | 17.29% ± 3.90% | 15.62% ± 3.07% | 11.73% ± 6.75% | 10.20% ± 4.70% | 9.74% ± 6.29% |
| 1 μM Iso + 100 μM IBMX | 25.8% ± 8.08% | 25.41% ± 8.86% | 26.9% ± 7.29% | 27.49% ± 6.27% | 24.6% ± 8.21% |
| 50 μM FsK | 18.73% ± 3.97% | 20.79% ± 4.6% | 22.82% ± 4.58% | 24.98% ± 3.69% | 23.4% ± 4.53% |
| 50 μM Fsk + 10 μM H89 | 26.72% ± 7.05% | 27.15% ± 8.66% | 28.15% ± 9.89% | 28.0% ± 6.89% | 28.77% ± 8.79% |
| 50 μM Fsk + 100 μM IBMX | 34.31% ± 13.16% | 33.42% ± 13.48% | 33.42% ± 13.03% | 34.16% ± 13.75% | 34.85% ± 13.52% |

|  | 11 | 12 | 13 | 14 | 15 |
|---|---|---|---|---|---|
| 1 μM Iso | 6.94% ± 1.93 | 2.26% ± 5.45% | 2.47% ± 6.06% | 2.27% ± 3.37% | 1.80% ± 5.84% |
| 1 μM Iso + 10 μM H89 | 7.99% ± 4.08% | 7.73% ± 3.38% | 6.60% ± 4.19% | 5.46% ± 2.77% | 5.37% ± 3.59% |
| 1 μM Iso + 100 μM IBMX | 27.68% ± 5.95% | 25.24% ± 6.85% | 25.99% ± 5.56% | 24.86% ± 6.02% | 25.92% ± 5.35% |
| 50 μM FsK | 24.46% ± 3.51% | 25.44% ± 2.14% | 24.97% ± 3.91% | 25.6% ± 4.31% | 27.0% ± 1.87% |
| 50 μM Fsk + 10 μM H89 | 30.11% ± 7.77% | 28.92% ± 8.35% | 29.54% ± 7.01% | 30.64% ± 7.81% | 31.14% ± 7.65% |
| 50 μM Fsk + 100 μM IBMX | 34.16% ± 15.2% | 35.09% ± 15.11% | 35.44% ± 14.71% | 35.43% ± 15.66% | 36.44% ± 16.43% |

|  | 16 | 17 | 18 | 19 | 20 |
|---|---|---|---|---|---|
| 1 μM Iso | 1.05% ± 5.87% | 1.29% ± 2.72% | 1.68% ± 6.12% | 2.52% ± 3.54% | 0.93% ± 4.45% |
| 1 μM Iso + 10 μM H89 | 3.37% ± 3.12% | 2.73% ± 6.59% | 3.98% ± 3.63 | 4.01% ± 1.59% | 5.10% ± 3.20% |
| 1 μM Iso + 100 μM IBMX | 25.77% ± 4.74% | 22.86% ± 6.32% | 20.58% ± 7.09% | 19.45% ± 8.36% | 20.2% ± 6.64% |
| 50 μM FsK | 25.84% ± 3.57% | 26.32% ± 1.66% | 25.94% ± 3.05% | 25.98% ± 2.13% | 25.51% ± 1.67% |
| 50 μM Fsk + 10 μM H89 | 31.51% ± 7.08% | 32.65% ± 6.2% | 30.65% ± 7.71% | 31.38% ± 6.57% | 32.19% ± 7.33 |
| 50 μM Fsk + 100 μM IBMX | 35.93% ± 16.26% | 35.6% ± 16.65% | 35.34% ± 15.77% | 35.87% ± 17.04% | 35.99% ± 17.19% |

TABLE 2

Average percent FRET response ± standard deviation at different time points for the high throughput analysis shown in FIG. 9.

|  | 0 sec. | 145 sec. | 290 sec. | 435 sec. | 580 sec. | 725 sec. |
| --- | --- | --- | --- | --- | --- | --- |
| HBSS | 2.09% ± 2.50% | 2.41% ± 2.16% | 1.46% ± 1.12% | 1.95% ± 1.74% | 2.15% ± 1.44% | 2.09% ± 1.26% |
| 1 μM ISO + 10 μM PRO | 0.142% ± 2.46% | 2.1% ± 2.07% | 0.978% ± 1.96% | 0.928% ± 1.42% | 0.457% ± 2.11% | 0.581% ± 1.29% |
| 1 μM ISO + 100 μM IBMX | 7.61% ± 3.19% | 8.1% ± 1.38% | 6.54% ± 1.37% | 3.73% ± 0.911% | 2.57% ± 1.33% | 1.83% ± 1.06% |
| 50 μM FSK | 9.73% ± 1.62% | 15.4% ± 1.92% | 17.9% ± 2.8% | 18.0% ± 2.22% | 18.2% ± 2.33% | 19.0% ± 2.2% |
| 50 μM FSK + 10 μM PRO | 9.05% ± 3.18% | 13.0% ± 3.17% | 14.8% ± 3.35% | 16.7% ± 3.33% | 16.8% ± 3.27% | 17.9% ± 3.63% |
| 50 μM FSK + 100 μM IBMX | 8.52% ± 3.25% | 15.6% ± 3.15% | 15.6% ± 2.2% | 18.1% ± 3.05% | 17.3% ± 2.33% | 18.2% ± 2.21% |
| 50 μM FSK + 10 μM H89 | 14.0% ± 3.65% | 19.9% ± 7.12% | 20.7% ± 2.47% | 21.7% ± 2.37% | 23.0% ± 2.31% | 24.1% ± 2.71% |
|  | 14.5% ± 2.0% | 18.5% ± 2.56% | 20.5% ± 2.9% | 21.9% ± 2.83% | 22.1% ± 2.46% | 23.2% ± 2.43% |

The invention claimed is:

1. A cAMP reporter comprising:
   (a) a donor moiety;
   (b) a polypeptide consisting of amino acids 149-881 of SEQ ID NO:1, which comprises a cAMP-binding domain of an exchange protein directly activated by cAMP (Epac), wherein the polypeptide is linked to the donor moiety;
   (c) an acceptor moiety linked to the polypeptide, wherein the donor moiety and the acceptor moiety exhibit a detectable resonance energy transfer when the donor moiety is excited;
   wherein each of the donor and acceptor moieties is a protein.

2. The cAMP reporter of claim 1 wherein at least one of the donor and acceptor moieties is a fluorescent protein.

3. The cAMP reporter of claim 1 wherein each of the donor and the acceptor moieties is a fluorescent protein.

4. The cAMP reporter of claim 1 wherein at least one of the donor and acceptor moieties is a luminescent protein.

5. The cAMP reporter of claim 1 wherein the acceptor moiety is selected from the group consisting of a fluorescent protein, a circularly permuted fluorescent protein, and a luminescent protein.

6. The cAMP reporter of claim 1 wherein the donor moiety is selected from the group consisting of a fluorescent protein, a circularly permuted fluorescent protein, and a luminescent protein.

7. The cAMP reporter of claim 1 wherein the donor moiety is a fluorescent protein selected from the group consisting of a green fluorescent protein (GFP), a red fluorescent protein (RFP), a yellow fluorescent protein (YFP), a blue fluorescent protein (BFP), a cyan fluorescent protein (CFP), and fluorescent mutants thereof.

8. The protein of claim 1 wherein the acceptor moiety is a luminescent protein.

9. The protein of claim 1 wherein the acceptor moiety is a luminescent protein selected from the group consisting of an aequorin, an obelin, a lux protein, a luciferase protein, a phycobiliprotein, a pholasin, and a green fluorescent protein.

10. The cAMP reporter of claim 1 further comprising a subcellular targeting sequence fused to the N-terminus of the donor moiety or the C-terminus of the acceptor moiety.

11. The cAMP reporter of claim 10 wherein the subcellular targeting sequence targets the reporter to a subcellular location selected from the group consisting of a plasma membrane, a nuclear membrane, an endoplasmic reticulum, a mitochondria, a mitochondrial matrix, a chloroplast, a medial trans-Golgi cisternae, a lumen of a lysosome, and a lumen of an endosome.

12. The cAMP reporter of claim 10 which comprises a subcellular targeting sequence selected from the group consisting of a plasma membrane targeting sequence comprising SEQ ID NO: 6, a nuclear localization signal sequence comprising SEQ ID NO: 5, a mitochondrial localization sequence comprising SEQ ID NO: 7, and a mitochondrial matrix targeting signal comprising SEQ ID NO: 8.

13. A cAMP reporter comprising:
   (a) a donor moiety;
   (b) a polypeptide consisting of amino acids 149-881 of SEQ ID NO:1, which comprises a cAMP-binding domain of an exchange protein directly activated by cAMP (Epac), wherein the polypeptide is linked to the donor moiety;
   (c) an acceptor moiety linked to the polypeptide, wherein the donor moiety and the acceptor moiety exhibit a detectable resonance energy transfer when the donor moiety is excited,
wherein the donor moiety is enhanced cyan fluorescent protein and the acceptor moiety is cpVenus L194.

14. A nucleic acid molecule which encodes a cAMP reporter comprising:
   (a) a donor moiety;
   (b) a polypeptide consisting of amino acids 149-881 of SEQ ID NO:1, which comprises a cAMP-binding domain of an exchange protein directly activated by cAMP (Epac), wherein the polypeptide is linked to the donor moiety;
   (c) an acceptor moiety linked to the polypeptide, wherein the donor moiety and the acceptor moiety exhibit a detectable resonance energy transfer when the donor moiety is excited;
   wherein each of the donor and acceptor moieties is a protein.

15. A nucleic acid molecule which encodes a cAMP reporter comprising:
   (a) a donor moiety;
   (b) a polypeptide consisting of amino acids 149-881 of SEQ ID NO:1, which comprises a cAMP-binding domain of an exchange protein directly activated by cAMP (Epac), wherein the polypeptide is linked to the donor moiety;
   (c) an acceptor moiety linked to the polypeptide, wherein the donor moiety and the acceptor moiety exhibit a detectable resonance energy transfer when the donor moiety is excited,
wherein the donor moiety is enhanced cyan fluorescent protein and the acceptor moiety is cpVenus L194.

16. A host cell comprising the nucleic acid molecule of claim 14.

17. A method for detecting a change in cAMP concentration, comprising:
   detecting a first resonance energy transfer of a cAMP reporter at a first time point, wherein the cAMP reporter comprises
      (a) a donor moiety;
      (b) a polypeptide consisting of amino acids 149-881 of SEQ ID NO:1,
   which comprises a cAMP-binding domain of an exchange protein directly activated by cAMP (Epac), wherein the polypeptide is linked to the donor moiety; and
      (c) an acceptor moiety linked to the polypeptide, wherein the donor moiety and the acceptor moiety exhibit a detectable resonance energy transfer when the donor moiety is excited, wherein each of the donor and acceptor moieties is a protein;
   detecting a second resonance energy transfer of the cAMP reporter at a second time point; and comparing the first and the second resonance energy transfers,
   wherein a difference between the first and the second resonance energy transfers reflects a change in cAMP concentration between the first and second time points.

18. The method of claim 17 wherein the first and second resonance energy transfers are detected by determining a property selected from the group consisting of a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

19. The method of claim 17 wherein the cAMP reporter is in a cell-free system.

20. The method of claim 17 wherein the cAMP reporter is in a cell.

21. The method of claim 20 wherein the cell is in vivo.

22. The method of claim 20 wherein the cell is in vitro.

23. The method of claim 20 wherein the cell is in a tissue sample.

24. The method of claim 20 wherein the cell is in a whole organ.

25. The method of claim 20 wherein the cell is in a well of a multi-well plate.

26. The method of claim 25 wherein each of a plurality of wells of the multi-well plate comprises a cell which comprises the cAMP reporter.

27. The method of claim 17 further comprising determining the second resonance energy transfer in the presence of a test compound.

28. The method of claim 20 wherein the first and second resonance energy transfers are detected using fluorescence activated cell sorting.

29. The method of claim 26 further comprising contacting each well of the plurality with a different test compound and determining second resonance energy transfers in the presence of the different test compounds.

30. A kit, comprising:
(a) a cAMP reporter comprising:
  (1) a donor moiety;
  (2) a polypeptide consisting of amino acids 149-881 of SEQ ID NO:1, which comprises a cAMP-binding domain of an exchange protein directly activated by cAMP (Epac), wherein the polypeptide is linked to the donor moiety;
  (3) an acceptor moiety linked to the polypeptide, wherein the donor moiety and the acceptor moiety exhibit a detectable resonance energy transfer when the donor moiety is excited, wherein each of the donor and acceptor moieties is a protein; and
(b) instructions for the method of claim 17.

31. The nucleic acid molecule of claim 14 wherein at least one of the donor and acceptor moieties is a fluorescent protein.

32. The nucleic acid molecule of claim 14 wherein each of the donor and the acceptor moieties is a fluorescent protein.

33. The nucleic acid molecule of claim 14 wherein at least one of the donor and acceptor moieties is a luminescent protein.

34. The nucleic acid molecule of claim 14 wherein the acceptor moiety is a circularly permuted fluorescent protein.

35. The nucleic acid molecule of claim 14 wherein the donor moiety is a circularly permuted fluorescent protein.

36. The nucleic acid molecule of claim 14 wherein the donor moiety is a fluorescent protein selected from the group consisting of a green fluorescent protein (GFP), a red fluorescent protein (RFP), a yellow fluorescent protein (YFP), a blue fluorescent protein (BFP), a cyan fluorescent protein (CFP), and fluorescent mutants thereof.

37. The nucleic acid molecule of claim 14 wherein the acceptor moiety is a luminescent protein selected from the group consisting of an aequorin, an obelin, a lux protein, a luciferase protein, a phycobiliprotein, a pholasin, and a green fluorescent protein.

38. The nucleic acid molecule of claim 14 wherein the cAMP reporter further comprises a subcellular targeting sequence fused to the 5'-terminus of the donor moiety or the 3'-terminus of the acceptor moiety.

39. The nucleic acid molecule of claim 38 wherein the subcellular targeting sequence targets the reporter to a subcellular location selected from the group consisting of a plasma membrane, a nuclear membrane, an endoplasmic reticulum, a mitochondria, a mitochondrial matrix, a chloroplast, a medial trans-Golgi cisternae, a lumen of a lysosome, and a lumen of an endosome.

40. The nucleic acid molecule of claim 38 wherein the cAMP reporter further comprises a subcellular targeting sequence selected from the group consisting of a plasma membrane targeting sequence comprising SEQ ID NO:6, a nuclear localization signal sequence comprising SEQ ID NO:5, a mitochondrial localization sequence comprising SEQ ID NO:7, and a mitochondrial matrix targeting signal comprising SEQ ID NO:8.

41. The nucleic acid molecule of claim 14 which is in an expression vector.

42. A method of producing a cAMP reporter, comprising:
culturing a host cell comprising an expression vector which comprises the nucleic acid molecule of claim 14 under conditions which permit expression of the cAMP reporter from the nucleic acid molecule; and
recovering the cAMP reporter.

43. A host cell comprising the nucleic acid molecule of claim 15.

44. The cAMP reporter of claim 1 wherein the acceptor moiety is citrine.

45. The cAMP reporter of claim 1 wherein the donor moiety is enhanced cyan fluorescent protein.

46. The cAMP reporter of claim 1 wherein the donor moiety is a cyan fluorescent protein.

47. The cAMP reporter of claim 1 wherein the acceptor moiety is a yellow fluorescent protein.

48. The cAMP reporter of claim 1 wherein the donor moiety is a cyan fluorescent protein and the acceptor moiety is a yellow fluorescent protein.

49. The cAMP reporter of claim 1 wherein the donor moiety is an enhanced cyan fluorescent protein and the acceptor moiety is a yellow fluorescent protein.

50. The cAMP reporter of claim 1 wherein the donor moiety is a cyan fluorescent protein and the acceptor moiety is citrine.

51. The cAMP reporter of claim 1 wherein the donor moiety is a cyan fluorescent protein and the acceptor moiety is cpVenus L194.

* * * * *